(12) United States Patent
Kratzberg et al.

(10) Patent No.: US 11,135,077 B2
(45) Date of Patent: Oct. 5, 2021

(54) METHOD OF AIR REDUCTION IN STENT GRAFT DELIVERY DEVICE

(71) Applicant: Cook Medical Technologies LLC, Bloomington, IN (US)

(72) Inventors: Jarin A. Kratzberg, West Lafayette, IN (US); Blayne A. Roeder, Bloomington, IN (US); Erik E. Rasmussen, Slagelse (DK); Tilo Kölbel, Hamburg (DE)

(73) Assignee: Cook Medical Technologies LLC, Bloomington, IN (US)

( * ) Notice: Subject to any disclaimer, the term of this patent is extended or adjusted under 35 U.S.C. 154(b) by 30 days.

(21) Appl. No.: 15/840,312

(22) Filed: Dec. 13, 2017

(65) Prior Publication Data
US 2018/0168838 A1    Jun. 21, 2018

Related U.S. Application Data

(60) Provisional application No. 62/435,182, filed on Dec. 16, 2016.

(51) Int. Cl.
*A61F 2/966* (2013.01)
*A61M 39/22* (2006.01)
*A61F 2/958* (2013.01)

(52) U.S. Cl.
CPC .......... *A61F 2/966* (2013.01); *A61M 39/225* (2013.01); *A61F 2/958* (2013.01)

(58) Field of Classification Search
CPC ........ A61F 2/966; A61F 2/958; A61M 39/225
See application file for complete search history.

(56) References Cited

U.S. PATENT DOCUMENTS

| | | |
|---|---|---|
| 6,106,497 A | 8/2000 | Wang |
| 6,645,197 B2 | 11/2003 | Garrison et al. |
| 7,803,177 B2 | 9/2010 | Hartley et al. |
| 7,867,270 B2 | 1/2011 | Hartley et al. |
| 8,709,061 B2 | 4/2014 | Greenberg et al. |
| 2001/0039411 A1* | 11/2001 | Johansson .......... A61B 5/14539 604/509 |

(Continued)

FOREIGN PATENT DOCUMENTS

| | | |
|---|---|---|
| WO | WO 2012/096687 A1 | 7/2012 |
| WO | WO 2016/172629 A1 | 10/2016 |

OTHER PUBLICATIONS

Tilo Kobel, Fiona Rohlffs,, Sabine Wipper, Sebastian Carpenter, Eike Seastian Debus, NikolarTsilimparis, Carbon Dioxide Flushing Techniques to Prevent Cerebral Arterial Air Embolism and Stroke During Tevar, Journal of Endovascular Therapy, 23(2), 393-395 (Year: 2016).*

(Continued)

*Primary Examiner* — Richard G Louis
(74) *Attorney, Agent, or Firm* — Crowell & Moring

(57) ABSTRACT

Methods of reducing air within a stent graft delivery device are disclosed, utilizing various flushing techniques. A port in a manifold that includes a pusher catheter coaxially disposed about a guide wire catheter is flushed. A portion in a sheath hub that excludes a longitudinally extended outer sheath coaxially disposed about the pusher catheter is flushed with a flushing fluid and/or a blood soluble gas, such as carbon dioxide. The guide wire catheter is also flushed.

23 Claims, 14 Drawing Sheets

(56) References Cited

U.S. PATENT DOCUMENTS

| | | | |
|---|---|---|---|
| 2002/0032486 A1* | 3/2002 | Lazarovitz | A61M 25/1011 623/23.67 |
| 2002/0052638 A1* | 5/2002 | Zadno-Azizi | A61B 17/12045 623/1.2 |
| 2003/0109886 A1* | 6/2003 | Keegan | A61F 2/966 606/108 |
| 2003/0176910 A1* | 9/2003 | Vrba | A61F 2/01 623/1.11 |
| 2003/0204237 A1 | 10/2003 | Krivoruchko et al. | |
| 2007/0181157 A1 | 8/2007 | Dadourian | |
| 2009/0182405 A1* | 7/2009 | Arnault De La Menardiere | A61F 2/856 623/1.11 |
| 2010/0125324 A1* | 5/2010 | Collins | A61M 25/007 623/1.11 |
| 2010/0222637 A1* | 9/2010 | Kassab | A61B 5/02152 600/17 |
| 2010/0222738 A1* | 9/2010 | Kassab | A61B 5/02152 604/99.04 |
| 2011/0270372 A1* | 11/2011 | Argentine | A61F 2/95 623/1.11 |
| 2014/0277403 A1* | 9/2014 | Peter | A61F 2/2415 623/2.11 |
| 2017/0042712 A1 | 2/2017 | Kölbel | |
| 2017/0143446 A1 | 5/2017 | Kölbel | |
| 2017/0367861 A1 | 12/2017 | Kölbel | |
| 2018/0110610 A1 | 4/2018 | Kölbel et al. | |
| 2019/0231567 A1 | 8/2019 | Kolbel | |

OTHER PUBLICATIONS

International Search Report and Written Opinion for PCT/US2017/066098, dated Mar. 23, 2018, 12 pages.
International Preliminary Report on Patentability for PCT/US2017/066098, dated Jun. 18, 2019, 4 pages.
Tilo Kölbel, et al., Carbon Dioxide Flushing Technique to Prevent Cerebral Arterial Air Embolism and Stroke During TEVAR, *Journal of Endovascular Therapy*, 2016, vol. 23(2), pp. 393-395.
Fiona Rohlffs, et al., Air Embolism During TEVAR: Carbon Dioxide Flushing Decreases the Amount of Gas Released From thoracic Stent-Grafts During Deployment, *Journal of Endovascular Therapy*, 2017, vol. 24(1), pp. 84-88.
Examination Report for EP Application No. 17823317.7, dated Jul. 10, 2020, 4 pages.

* cited by examiner

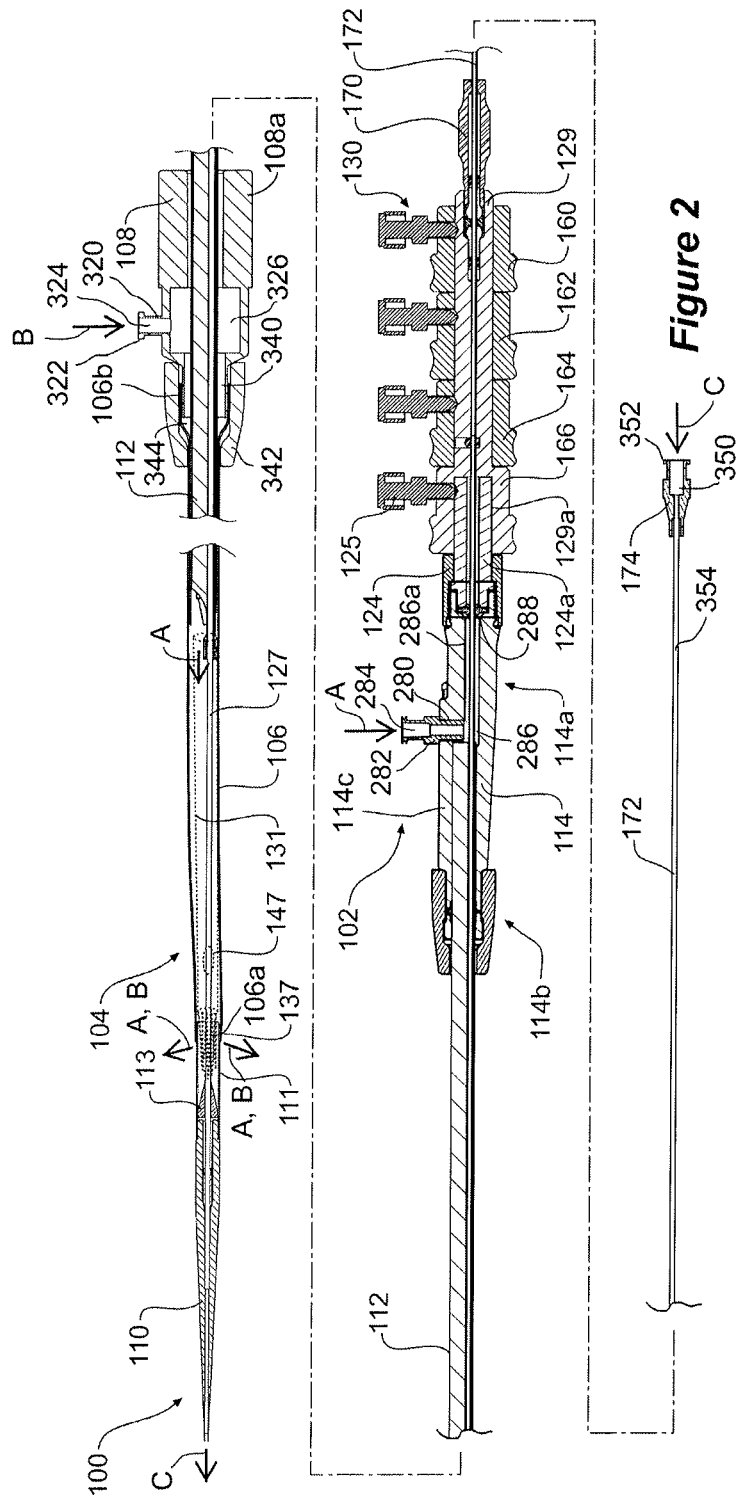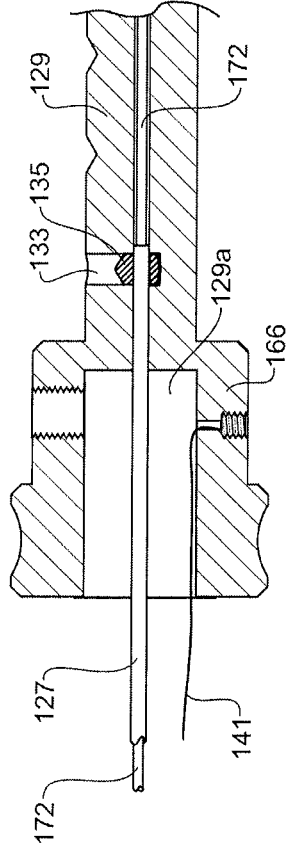
Figure 2
Figure 2A

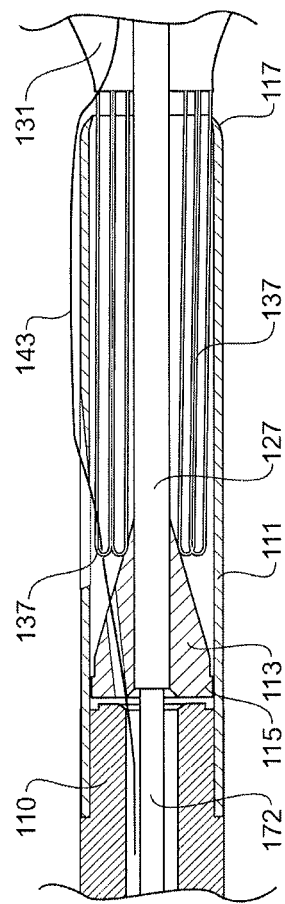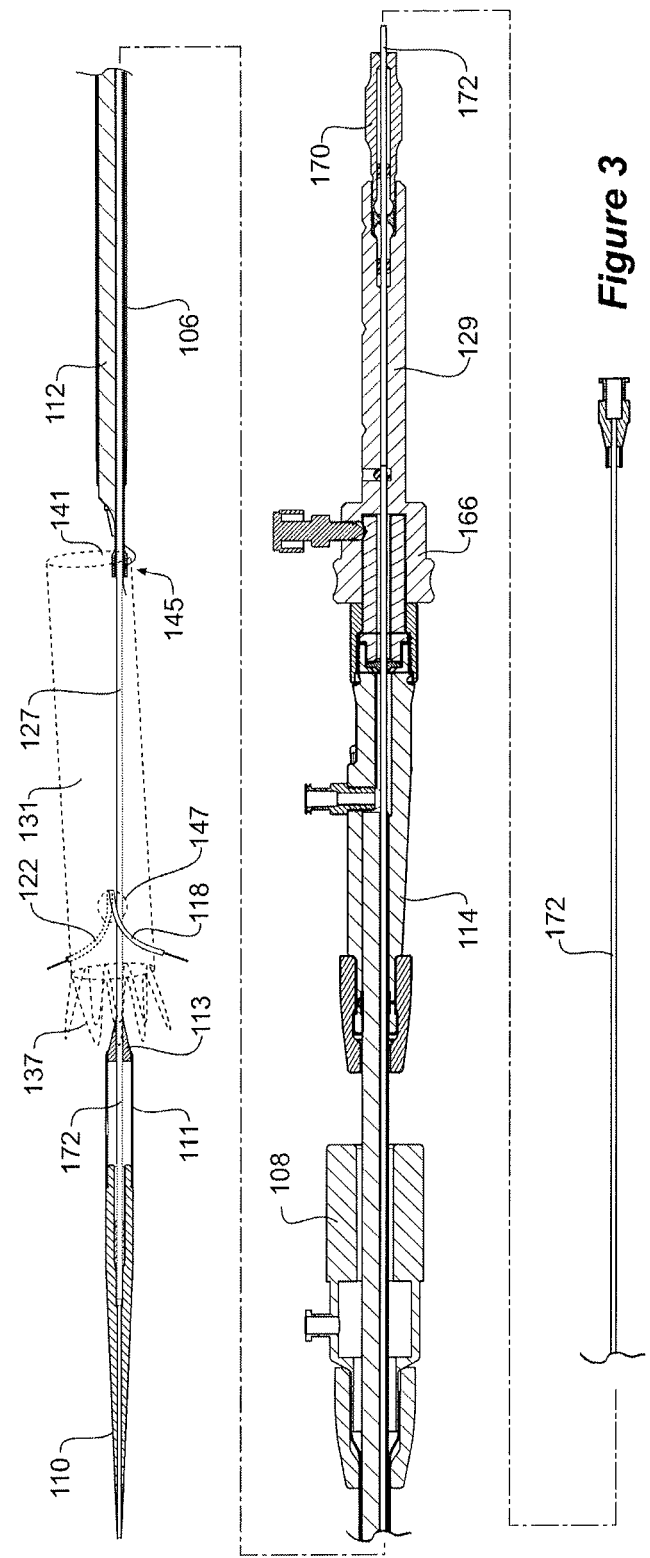

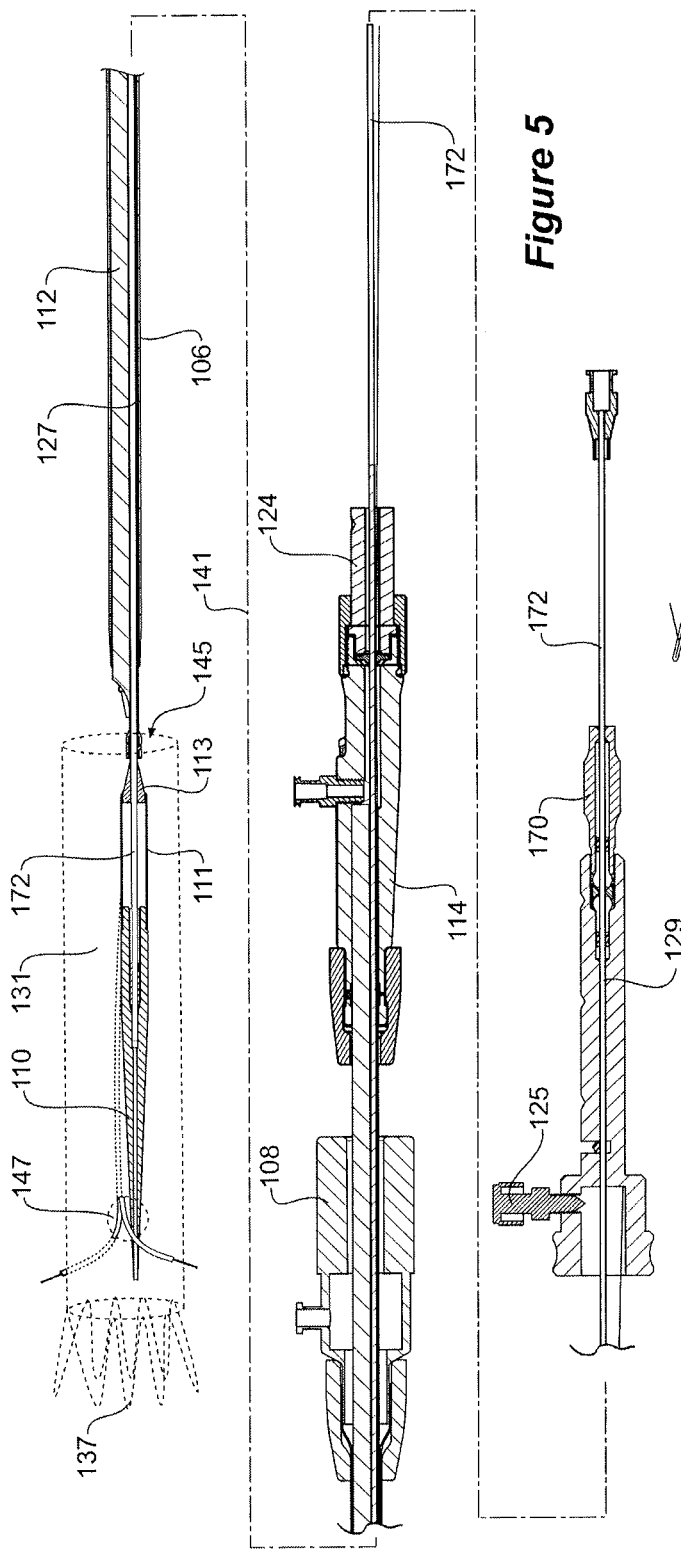
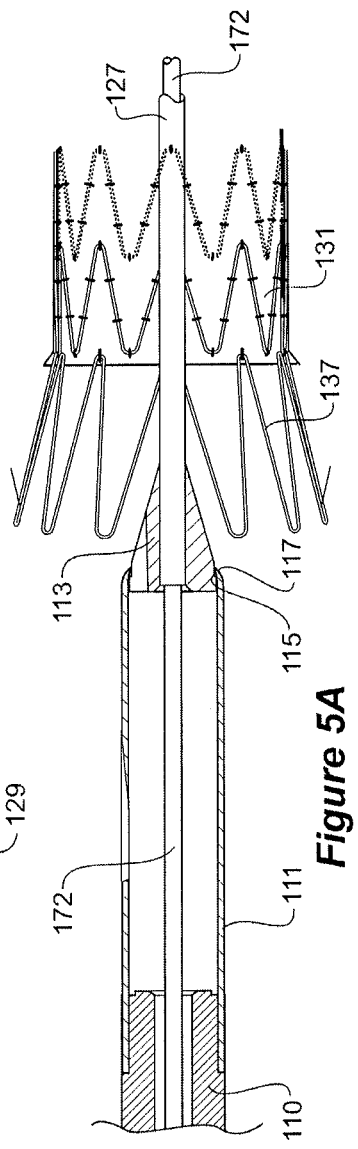
Figure 5
Figure 5A

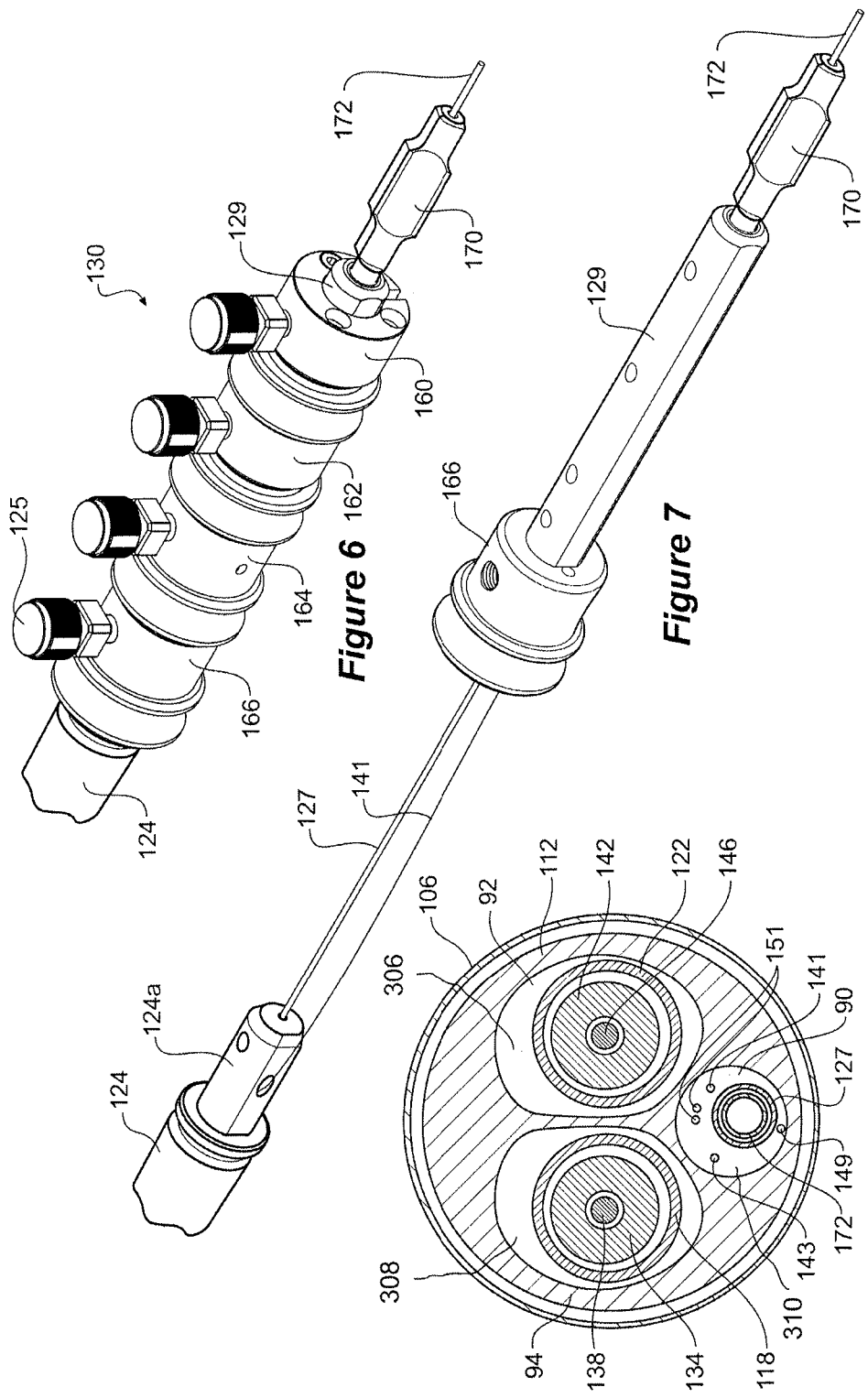

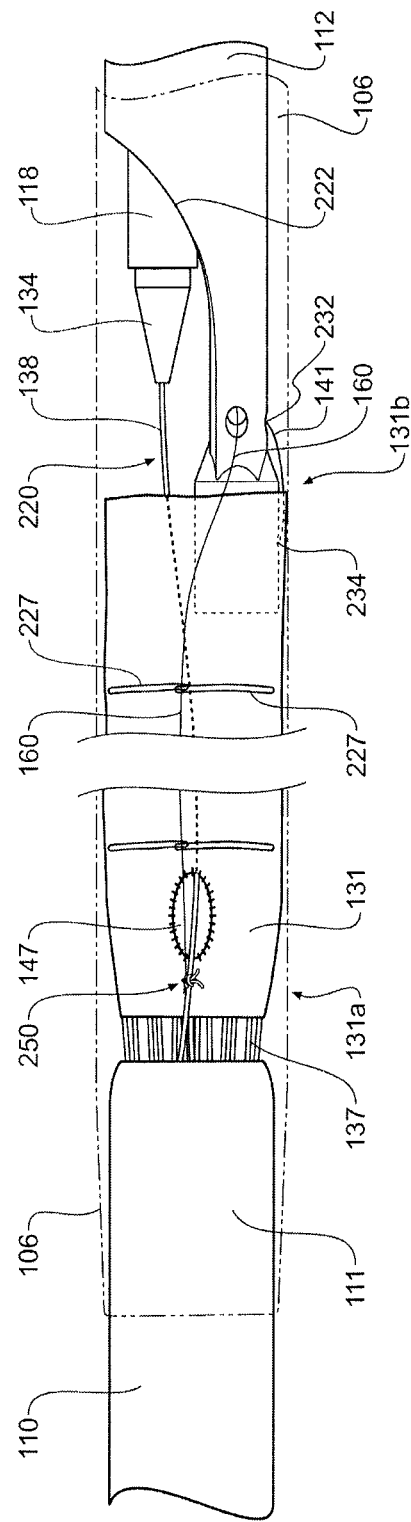
*Figure 12*
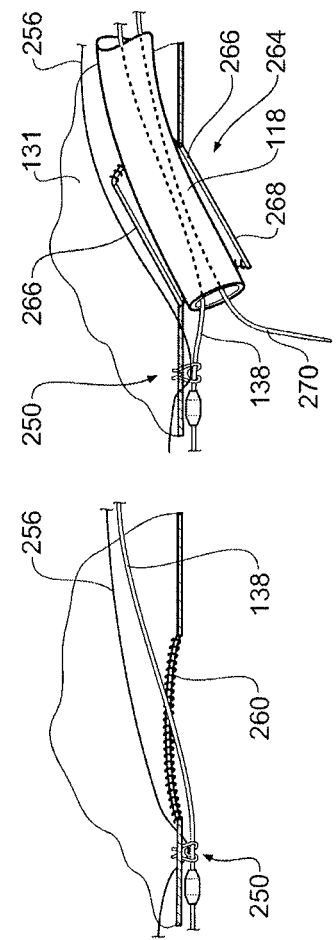
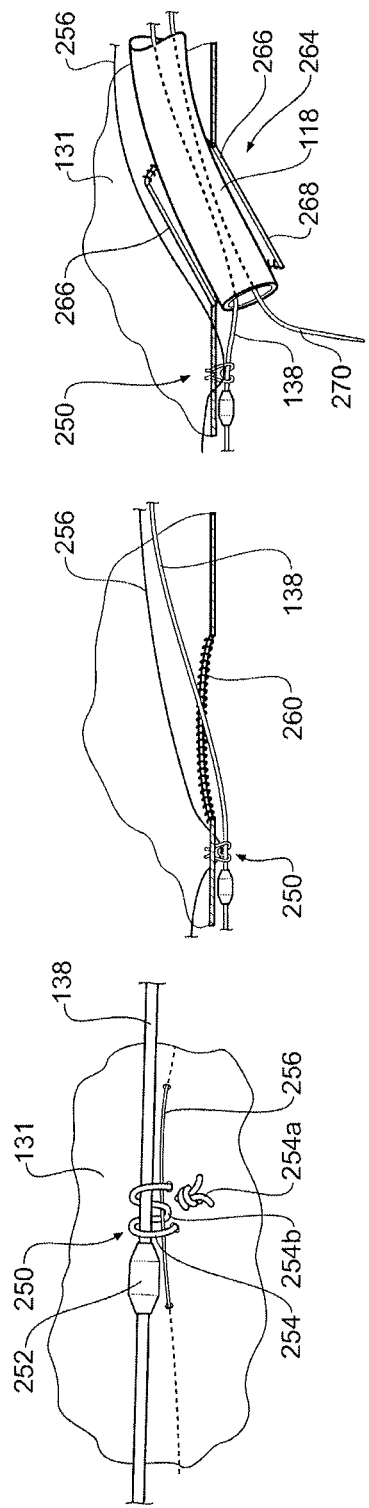
*Figure 15*
*Figure 14*
*Figure 13*

METHOD OF AIR REDUCTION IN STENT GRAFT DELIVERY DEVICE

CROSS-REFERENCE TO RELATED APPLICATIONS

This application claims priority and the benefit of U.S. provisional Patent Application Ser. No. 62/435,182, filed Dec. 16, 2016, which is incorporated herein by reference in its entirety.

BACKGROUND

The present disclosure relates generally to methods of reducing air in medical devices, and, more particularly, to methods for flushing trapped air from stent graft delivery devices, catheters or other medical devices.

Endovascular methods have been proposed for treatment of diseases of the aorta such as aortic dissection and aortic aneurysm. Using prostheses, such as stent grafts, to treat aneurysms is common in the medical field. Stent grafts are deployed using stent graft deployment systems by accessing a vasculature with a small incision in the skin and guiding a delivery system to the target area. This endoluminal delivery is less invasive and generally preferred over more intrusive forms of surgery.

Stent graft deployment systems are known to carry trapped air in the various spaces. When introduced into the patient, the trapped air may cause air embolism within the patient. Air emboli that may be introduced during endovascular methods can be detrimental to a patient's outcome, often attributing to additional complications. There may be a higher risk of air embolism with trapped air within the stent graft deployment systems, especially in larger bore devices. Before such deployment systems are introduced into a patient, saline may be introduced for flushing aspects of the deployment system to reduce the amount of trapped air. Even so, more care must be taken to further reduce the amount of trapped air from stent graft deployment systems in order to minimize any potential risk of air emboli into the patient's vasculature.

SUMMARY

A method of reducing air within a stent graft delivery device is described herein. The method includes one or more of the following steps. A step includes providing a stent graft delivery device comprising a guide wire catheter and a pusher catheter coaxially disposed over the guide wire catheter. The pusher catheter is arranged relative to the guide wire catheter to define a stent graft retention region. A manifold includes a manifold passageway longitudinally receiving the pusher catheter. A sheath hub includes a hub passageway longitudinally receiving the pusher catheter. A sheath arrangement longitudinally extends from the sheath hub toward a proximal end of the guide wire catheter. The sheath arrangement is coaxial with and surrounds the guide wire catheter and the pusher catheter. A first fluid port is defined by the manifold and is in communication with the manifold passageway and the pusher lumen. A second fluid port is defined by the sheath hub and is in communication with the hub passageway and an annular space defined between the sheath arrangement and the pusher catheter. A third fluid port is at a distal end of the guide wire catheter and is in communication with a guide wire lumen that longitudinally extends within the guide wire catheter. A step includes flushing a first liquid within the first fluid port. The first liquid traverses the manifold passageway, and traverses proximally through the pusher lumen, through a proximal end opening of the pusher catheter, and into the stent graft retention region. At least a partial amount of first fluid exits the stent graft retention region at a proximal end of the sheath arrangement. A step includes flushing a gas within the second fluid port, and after a period of time subsequently flushing a second liquid within the second fluid port. Each of the gas and the second liquid traverses the hub passageway, and traverses proximally through the annular space and the stent graft retention region. At least a partial amount of gas and at least a partial amount of second fluid exit the stent graft retention region at a proximal end of the sheath arrangement. A step includes flushing a third liquid within the third fluid port. The third liquid traverses proximally through the guide wire lumen. At least a partial amount of third fluid exits out of the proximal end of the guide wire catheter. Less than 0.2 ml of air is present in the stent graft delivery device after the flushing.

Another example of a method of reducing air within a stent graft delivery device is provided. The method includes one or more of the following steps. A step includes providing a stent graft delivery device comprising a guide wire catheter, a dilator at a proximal end of the guide wire catheter, a pusher catheter coaxially disposed over the guide wire catheter, a proximal end of the pusher catheter spaced distally from the dilator to define a stent graft retention region therebetween, a manifold longitudinally receiving the pusher catheter, a sheath hub longitudinally receiving the pusher catheter, and a sheath arrangement longitudinally extending from the sheath hub toward the dilator, the sheath arrangement being coaxial with and surrounding the guide wire catheter and the pusher catheter, wherein a manifold port is defined by the manifold and in communication with the pusher lumen, a sheath hub port is defined by the sheath hub and in communication with an annular space defined between the sheath arrangement and the pusher catheter. A step includes flushing a first fluid within the manifold port, the first fluid traversing proximally through the pusher lumen, the proximal end of the pusher catheter, and into the stent graft retention region, and exiting the stent graft retention region at a proximal end of the sheath arrangement. A step includes flushing a second fluid within the sheath hub port, the second fluid comprising a blood soluble gas, the second fluid traversing proximally in the annular space and into the stent graft retention region, and exiting the stent graft retention region at the proximal end of the sheath arrangement. A step includes flushing a third fluid within the sheath hub port, the third fluid traversing proximally in the annular space and into the stent graft retention region, and exiting the stent graft retention region at the proximal end of the sheath arrangement. A step includes flushing a fourth fluid within a distal end opening of the guide wire catheter, the fourth fluid traversing proximally through a guide wire lumen that extends longitudinally within the guide wire catheter and exiting out of the proximal end of the guide wire catheter, whereby the flushing steps contribute to a removal of air present in the stent graft delivery device.

Also described is another example of a method of reducing air within a stent graft delivery device. The method includes one or more of the following steps. A step includes providing a stent graft delivery device comprising a guide wire catheter, a dilator at a proximal end of the guide wire catheter, a pusher catheter coaxially disposed over the guide wire catheter, a proximal end opening of the pusher catheter spaced distally from the dilator to define a stent graft retention region therebetween, a manifold longitudinally receiving the pusher catheter, a sheath hub longitudinally receiving the pusher catheter, and a sheath arrangement longitudinally extending from the sheath hub toward the dilator, the sheath arrangement being coaxial with and surrounding the guide wire catheter and the pusher catheter, wherein a manifold port is defined by the manifold and in communication with the manifold passageway and the pusher lumen, a sheath hub port is defined by the sheath hub and in communication with the hub passageway and an annular space defined between the sheath arrangement and the pusher catheter. A step includes introducing a first fluid of saline within the manifold port such that the first fluid of saline traverses the manifold passageway, proximally through the pusher lumen, through the proximal end opening of the pusher catheter, and into the stent graft retention region, and exits the stent graft retention region at a proximal end of the sheath arrangement. A step includes introducing a second fluid of carbon dioxide within the sheath hub port such that the second fluid of carbon dioxide traverses the hub passageway and proximally in the annular space, and into the stent graft retention region, and exits the stent graft retention region at the proximal end of the sheath arrangement. A step includes introducing a third fluid of saline within the sheath hub port after the introducing a second fluid of carbon dioxide step such that the third fluid of saline traverses the hub passageway, proximally in the annular space, and into the stent graft retention region, and exits the stent graft retention region at the proximal end of the sheath arrangement. A step includes introducing a fourth fluid of saline within a distal end opening of the guide wire catheter such that the fourth fluid of saline traverses proximally through a guide wire lumen that longitudinally extends within the guide wire catheter and exits out of the proximal end of the guide wire catheter, whereby less than 0.14 ml of air is present in the stent graft delivery device.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 2 is a longitudinal cross sectional view of the stent graft delivery device of FIG. 1.

FIG. 2A is a partial longitudinal cross sectional view of the stent graft delivery device of FIG. 1 and in particular a detail of a part of a distal handle portion.

FIG. 2B is a partial longitudinal cross sectional view of the stent graft delivery device of FIG. 1 and in particular a detail of a part of a nose cone dilator and capsule with a distal retrieval taper.

FIG. 3 is a longitudinal cross sectional view of the stent graft delivery device of FIG. 1 in a first partially activated condition.

FIG. 5 is a longitudinal cross sectional view of the stent graft delivery device of FIG. 4.

FIG. 5A is a partial longitudinal cross sectional view of the stent graft delivery device of FIG. 1, and in particular a detail of a part of a nose cone dilator and capsule with a distal retrieval taper in its distal position.

FIG. 6 is a perspective view of part of a handle of the stent graft delivery device of FIG. 1.

FIG. 7 is a perspective view of the handle in FIG. 6 in an activated condition.

FIG. 8 is a transverse cross sectional view of the pusher catheter portion of the stent graft delivery device of FIG. 1 along the line 8-8'.

FIG. 12 shows a schematic detailed side view of the stent graft retained on the delivery device.

FIG. 13 shows a method of releasable retention of the indwelling guide wire.

FIGS. 14 and 15 show two embodiments of fenestrations suitable for the stent graft delivery device.

DETAILED DESCRIPTION OF THE PREFERRED EMBODIMENTS

Described herein are methods for reducing air within stent graft delivery devices by flushing various lumens. Accordingly, any potential risk of air emboli related events and complications that may occur during endovascular procedures is reduced. With the prescribed methods, substantial amounts of air may be removed from three major air containing regions of a delivery device: an outer sheath, an inner catheter, and a wire guide catheter. In particular, the inner catheter (also referred to as the pusher catheter) is disposed within an outer sheath and coaxially over the wire guide catheter and extends from a manifold. The manifold includes a fluid port that is used for flushing the lumen of the inner catheter. The outer sheath extends from a hub that includes another fluid port, while the wire guide catheter includes another fluid port. The use of a flushing fluid, such as saline, and a high blood soluble gas, such as carbon dioxide, in the ports has been found beneficial in driving out the majority of the air within the delivery device.

In the present application, the term "proximal" when referring to a delivery device or stent graft refers to a direction that is farthest away from an operator using a delivery device and closest to the aorta, while the term "distal" refers to a direction that is generally closest to the operator using the delivery device. The distal and proximal ends of a delivery device may also be referred to as an introduction end of the delivery device and an operator end of the delivery device, respectively. The term "operator end" of the delivery device is that portion of the device that is intended to remain outside of a patient during a procedure. The term "introduction end" of the delivery device, which is opposite to the operator end, is that portion of the device that is intended to be inserted within a patient during a procedure.

Figure 1:
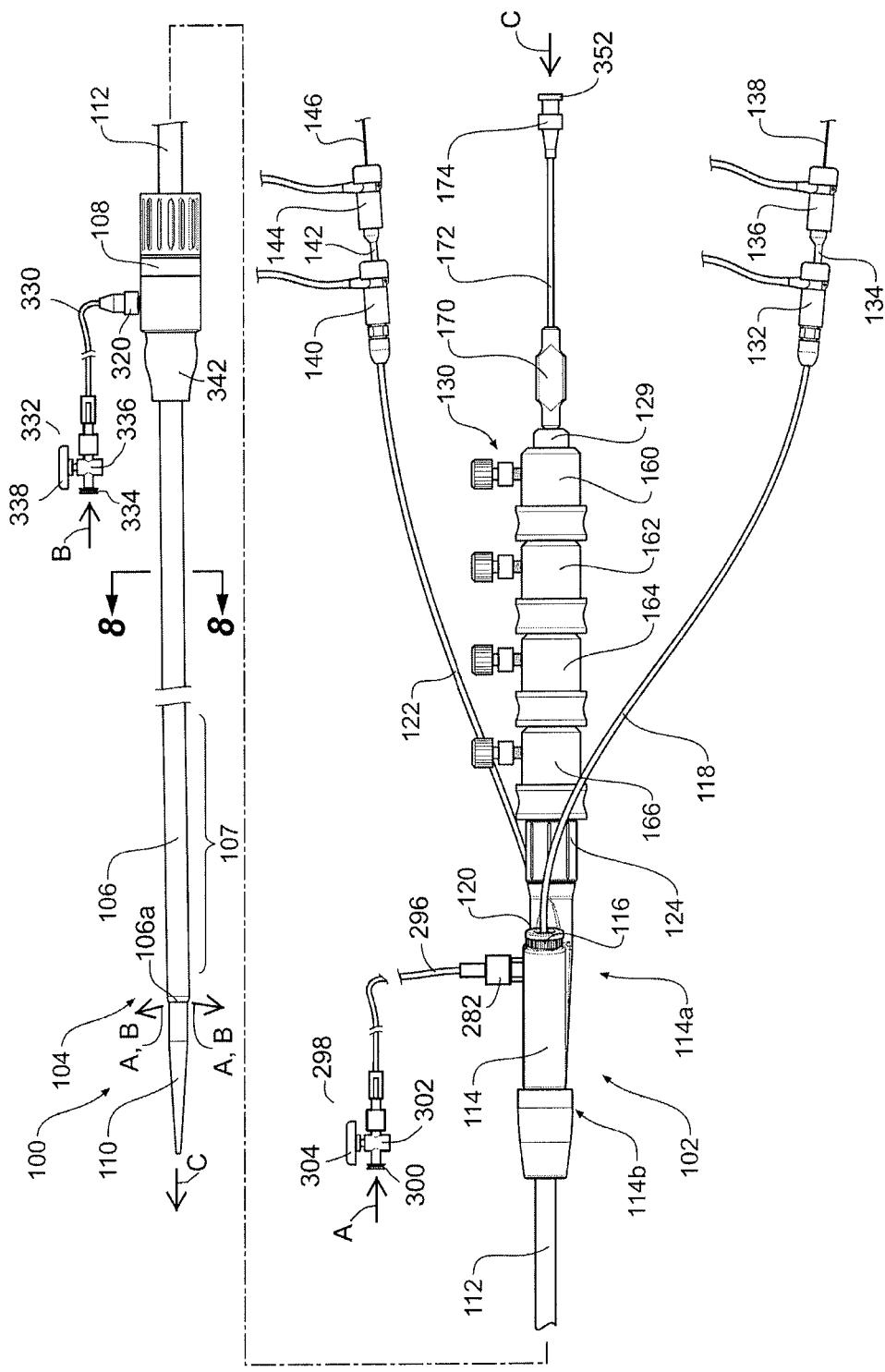
FIG. 1 illustrates an example of a stent graft delivery device.

FIGS. 1-2 depict an example of a pre-loaded stent graft delivery device 100. The delivery device 100 includes a handle and manifold assembly 102 and an introduction portion 104 intended to be deployed into the patient by the known Seldinger method. More specifically, the introduction section 104 includes an outer sheath 106 extending from a sheath hub 108 to a top cap assembly 110. A stent graft 131 is retained within the outer sheath 106 in a stent retention region 107 just distal of the top cap assembly 110.

The sheath hub 108 is positioned over a pusher catheter 112, which extends from and is connected into a manifold 114 as discussed in more detail below. The manifold 114 has a proximal end 114b into which is affixed the pusher catheter 112 and two access ports 116, 120 at its distal end 114a. With additional reference to FIG. 11, the access port 116 is shown having a hemostatic seal 119 and is for a first access sheath 118, and the access port 120 is shown having a hemostatic seal 121 is for a second access sheath 122. A handle assembly 130 is coupled at the distal end 114a of the manifold 114. The handle assembly 130 is shown including trigger wire release mechanisms and may be separated into two parts as discussed below.

The access sheath 118 extends distally to a hemostatic seal 132, and a dilator 134 is shown extending through the hemostatic seal 132. The dilator 134 may include a dilator hemostatic seal 136 through which extends an indwelling guide wire 138. The access sheath 122 extends distally to a hemostatic seal 140, and a dilator 142 is shown extending through the hemostatic seal 142. The dilator 142 may include a dilator hemostatic seal 144 through which extends an indwelling guide wire 146.

The handle assembly 130 may include a proximal handle portion 124, which is affixed to the rear of the manifold 114. The handle assembly 130 also may include a distal handle portion 129. The distal handle portion 129 may include a proximal axial recess 129a which fits over a distal extension 124a of the proximal handle portion 124 and a locking screw 125 that releasably locks the two handle portions together.

Trigger wire release mechanisms are shown releasably coupled onto the distal handle portion 129 of the handle assembly 130. With additional reference to FIG. 6, starting from the distal end of the distal handle portion 129, a trigger wire release 160 is for the release of the stabilization retention of indwelling guide wires as will be discussed below. A trigger wire release 162 is for diameter reducing ties as will be discussed below. A trigger wire release 164 is for a retention trigger wire for the exposed stent in a capsule 111 as will be discussed below. A trigger wire release mechanism 166 is for trigger wire 141 for distal retention of the distal end 145 of the stent graft 131 as will be discussed below. Trigger wire release mechanism 166 may also be part of the distal portion of the handle 129 and is thus configured to move together as a unit. A pin vice 170 is at a distal end of the handle assembly 130 and a guide wire catheter 172 for the delivery device extends through the pin vice 170. The pin vice 170 may be locked and may be released for selective longitudinal movement of the guide wire catheter 172 with respect to the distal portion of the handle assembly 130. A distal end of the guide wire catheter 172 terminates in a luer connector 174 to enable flushing liquid and radiopaque medium to be deployed through the delivery device.

In FIG. 2, the introduction portion 104 of the stent graft delivery device 100 may include the top cap assembly 110. The top cap assembly. 110 may include a nose cone dilator 110a alone, or a distally opening capsule 111 at a distal end of the nose cone dilator 110a for the receipt of an exposed stent 137 of the stent graft 131. The nose cone dilator 110 and the capsule 111 may be affixed to another to define a top cap assembly. The capsule 111 may have a slightly in-turned or tapered distal end 117 (see FIGS. 2B and 5A). This has two purposes, a first is to assist with engagement of the sheath 106 of the delivery device when the top cap assembly 110 is retracted into the sheath 106, and a second is to prevent complete withdrawal of a distal retrieval taper device 113 from the capsule 111 as will be discussed below. The guide wire catheter 172 extends from the handle assembly 130 to the nose cone dilator 110a. To this end, the guide wire catheter 172 is extended proximally through and fastened to the nose cone dilator 110a at a proximal end of the guide wire catheter 172 and is extended distally through the handle assembly 130. The pin vice 170 at the distal end of the distal handle portion 129 locks movement of the guide wire catheter 172 with respect to the distal portion of the handle 129 and can be loosened to allow relative motion between these components as discussed below.

The stent graft 131, shown in FIG. 2, for instance, includes a tubular body of a biocompatible graft material such as Dacron, expanded PTFE or Thoralon, a polyurethane material. The stent graft 131 is supported by self-expanding stents (not shown for clarity). The proximally extending exposed stent 137 assists with providing infrarenal fixation of the deployed stent graft. The stent graft 131 may include fenestrations (two fenestrations 147 shown) which are provided to give access to the renal arteries. The stent graft 131 is retained on the delivery device 100 by proximal retention of the exposed stent 137 into the capsule 111 of the delivery device and distally by the trigger wire retention 141 as will be discussed in detail below. Diameter reducing ties can be used to hold the stent graft in a diameter reduced condition during the initial catheterization of a side branch because it may still be necessary to move the stent graft proximally, distally or rotationally. In the diameter reduced condition, movement of the stent graft 131 is still possible, whereas when released to full diameter this may not be possible.

As can be seen particularly in FIGS. 5 and 5A, the distal retrieval taper device 113 fits coaxially around the guide wire catheter 172 and may move longitudinally along the guide wire catheter. A retrieval catheter 127 is mounted coaxially around the guide wire catheter 172 and may move longitudinally along the guide wire catheter 172. A proximal end of the retrieval catheter 127 may be affixed to the distal retrieval taper device 113. FIG. 2A shows detail of the mounting of the retrieval catheter 127 into the distal handle portion 129. For example, a distal end of the retrieval catheter 127 may be affixed to the distal handle portion 129 at a transverse aperture 133 extending into the distal handle portion 129 by a suitable adhesive 135. For this purpose, apertures 133 are provided into the handle and adhesive is applied through these apertures.

Turning back to FIGS. 5 and 5A, the distal retrieval taper device 113 includes an enlarged shoulder 115 at its proximal end. The shoulder is sized so that it is of greater diameter than the smallest part of the in-turned distal end 117 of the capsule 111. By this arrangement, the distal retrieval taper device 113 may move through the capsule 111 but may not be fully removed from the capsule 111. Movement of the guide wire catheter 172 proximally with respect to the distal handle portion 129, after release of the pin vice 170, will move the nose cone dilator 110a and the capsule 111 with respect to the distal retrieval taper device 113 with the effect that the distal retrieval taper device 113 extends distally from the capsule 111 in its final extended position as shown in FIG. 5A, thereby providing a smooth tapered surface for retrieval of the nose cone dilator through the stent graft. Locking of the pin vice 170 after the distal retrieval taper 113 has been moved to the distal end of the capsule 111 ensures that all of the distal retrieval taper, the capsule, the nose cone dilator and the distal handle portion all move together.

By this arrangement, the nose cone dilator 110a may be moved to a distal position with respect to fenestrations in the stent graft 131 so that the nose cone dilator 110a and the capsule 111 does not interfere with the deployment of side branch covered or uncovered stent grafts through such fenestrations nor does any subsequent retraction of the nose cone dilator 110a interfere with the deployed of side branch side branch covered or uncovered stent grafts. The use of the stabilization retention of the indwelling guide wire is particularly discussed therein.

As can be seen particularly in FIG. 8, which is a transverse cross section along the line 8-8' in FIG. 1, the pusher catheter 112 is surrounded by the outer sheath 106. The pusher catheter 112 may have one or more pusher longitudinally extending lumens, although three are shown. A first lumen is the guide wire lumen 90 and may be offset from the center of the pusher catheter 112 to allow for two auxiliary lumens 92 and 94. Passing through the guide wire lumen 90 are the guide wire catheter 172 and the retrieval catheter 127 coaxially around the guide wire catheter. Also in the guide wire lumen 90 are the trigger wires for the diameter reducing ties 149, the top capsule 143, the distal retention of the distal end 145 and the auxiliary guide wire stabilization 151. Passing through the auxiliary lumen 94 are the access sheath 118, the dilator 134, and the guide wire 138 in a coaxial relationship. Passing through the auxiliary lumen 92 are the access sheath 122, the dilator 142, and guide wire 146 in a coaxially relationship. The manifold and the pusher catheter arrangement may accommodate a single lumen similarly situated as the guide wire lumen 90.

Figure 9:
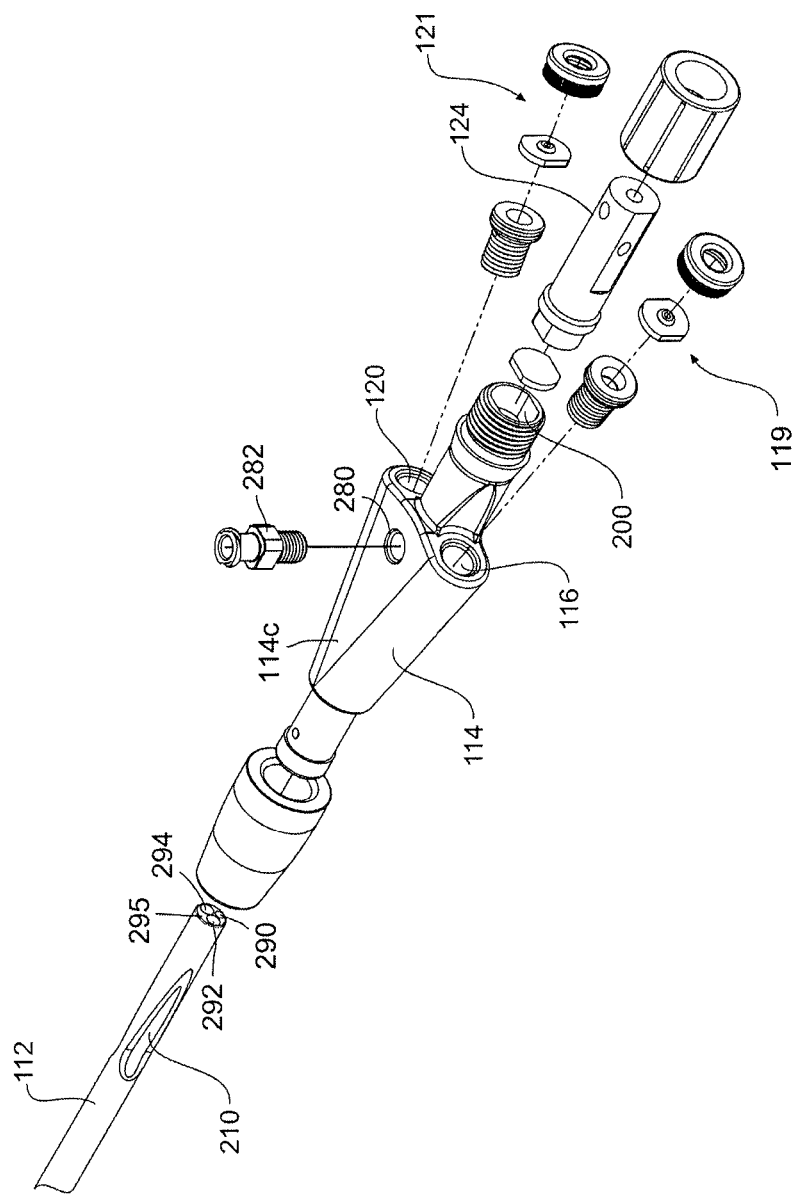
FIG. 9 is an exploded view of a manifold of an example of a stent graft delivery device.
Figure 10A:
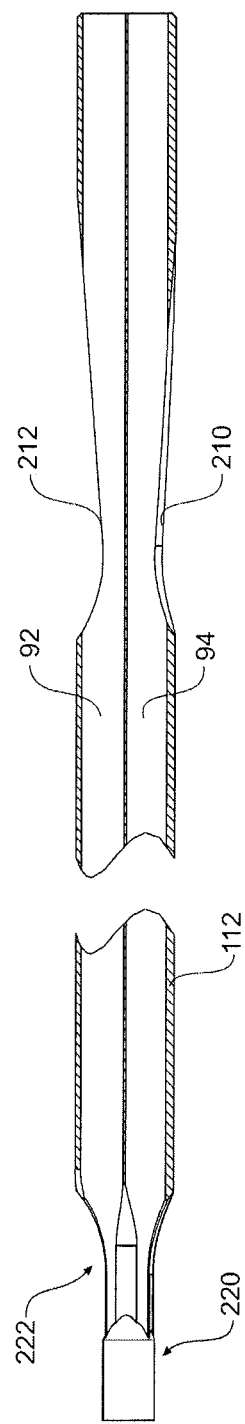
FIGS. 10A to 10D illustrate various views of a pusher catheter of an example of a stent graft delivery device.
Figure 10B:
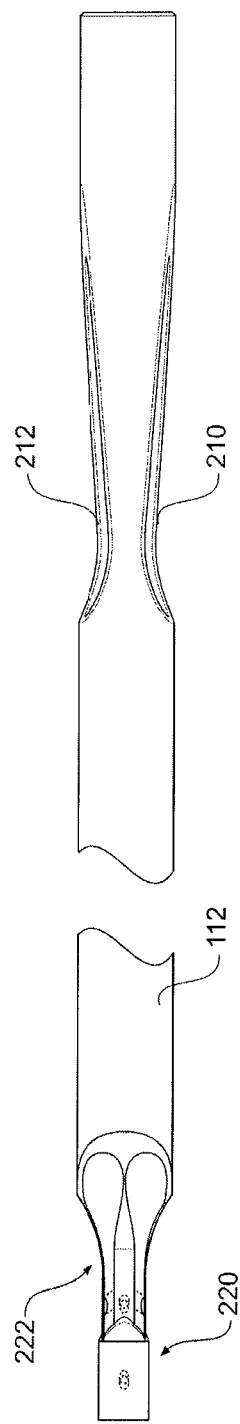
Figure 10C:
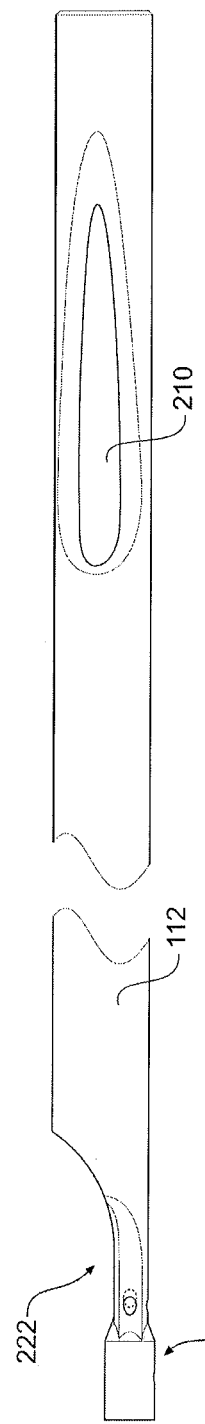
Figure 10D:
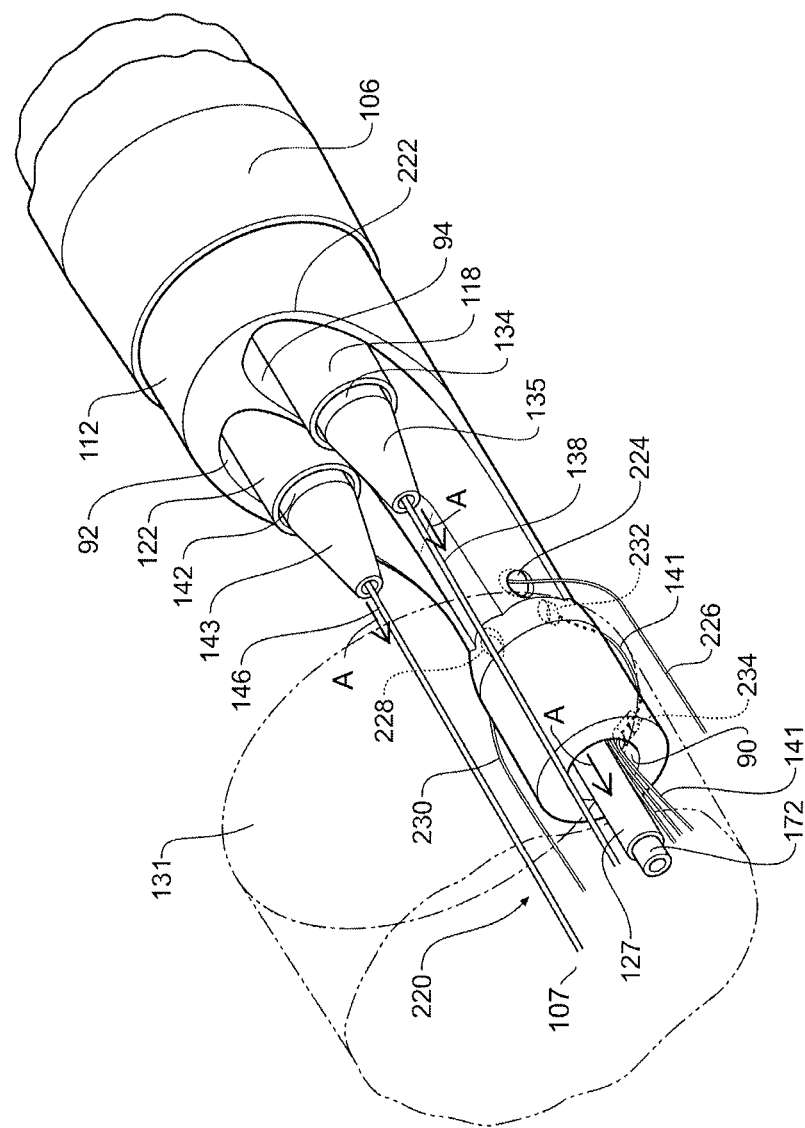
Figure 11:
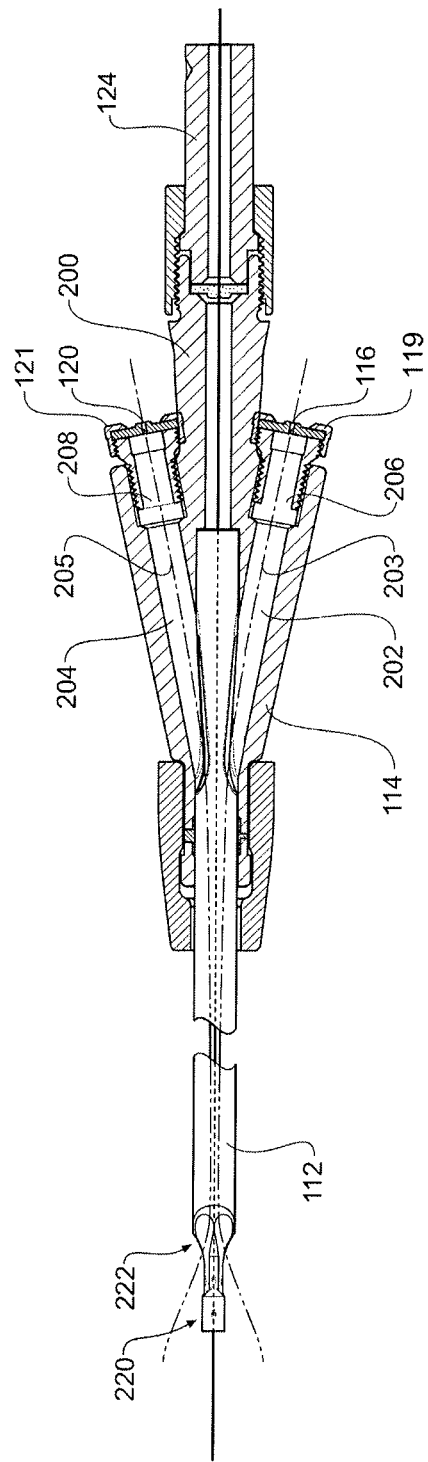
FIG. 11 is a cross sectional view of an assembly of a manifold and pusher catheter of an example stent graft delivery device.

In FIGS. 9-11, the manifold 114 and the pusher catheter 111 are shown in more detail. The manifold 114 has a through bore 200 and angled side ports 202 and 204. As previously described, the pusher catheter 111 is shown having three lumens, the guide wire lumen 90 off-set from the center of the pusher catheter to allow for two auxiliary lumens 94 and 92. As can be seen in FIGS. 10A to 10C, the pusher catheter 112 may include two side apertures 210 and 212, which open from the side of the pusher catheter 112 into the respective lumens 92 and 94. These side apertures are elongate and tapered towards the distal end. When the pusher catheter 112 is pushed into the through bore 200 of the manifold 114 the side apertures 210, 212 in the pusher catheter are aligned with the respective angled side ports 202, 204, thereby providing an uninterrupted lumen from the access port 116 for the first access sheath 118 into the pusher auxiliary lumen 94 along the dotted line 203 and from access port 120 for a second access sheath 122 into the pusher auxiliary lumen 92 along the dotted line 205.

Further in FIGS. 10A to 10, a proximal end of the pusher catheter 112 includes an attachment boss 220 to provide an exit port for the guide wire lumen 90 and a scalloped end 222 to provide exit ports for the two auxiliary lumens 92, 94. The guide wire lumen 90 opens out at the proximal end of the attachment boss 220. Each side of the attachment boss 220 includes apertures for trigger wires. Aperture 224 is for trigger wire 226, which is used for the diameter reducing ties on one side of the stent graft 131. A corresponding aperture 228 and the other side of the attachment boss 220 are for the trigger wire 230 for the other side of the stent graft 131. Trigger wire 141 extends out of aperture 232 in the attachment boss 220 and engages into the stent graft 131 before re-entering the attachment boss at aperture 234 and exiting the guide wire lumen 90 at the proximal end of the pusher catheter 112. Extending out of the two auxiliary lumens 92 and 94 are the auxiliary catheters 122 and 118 respectively. From the proximal ends of the respective auxiliary catheters 118 and 122 extend dilators 134 and 142. Dilator tips 135, 143 are shown at proximal ends of the respective dilators 134, 142. The auxiliary guide wires 138 and 146 extend through the dilators.

FIG. 12 shows detail of the stent graft 131 and its retention system in the region 107. In particular, there is detail shown of the distal attachment, the diameter reducing ties and the proximal retention. The stent graft 131 is retained within the outer sheath 106 (in dashed lines) and concentrically around the guide wire catheter 172 and retrieval catheter 127. The fenestration 147 is shown towards the proximal end 131a of the stent graft 131. In use, the stent graft 131 is deployed so that the fenestration is substantially aligned with a branch or renal artery and intended for catheterization through the branch or renal artery for the deployment of a covered or uncovered side branch stent or stent graft into the branch or renal artery. In its ready to deploy condition the proximally extending exposed stent 137 is received into the capsule 111 at the distal end of the nose cone dilator 110a. A distal end 131b of the stent graft 131 is retained to the attachment boss 220 at the proximal end of the pusher catheter 112. Trigger wire 141 engages the distal end 131b of the stent graft 131. Trigger wire 141 extends out of aperture 232 in the attachment boss 220 and engages into the stent graft 131 before re-entering the attachment boss through aperture 234 into the guide wire lumen 90 and exiting the guide wire lumen 90 at the proximal end of the pusher catheter 112. At its distal end the trigger wire 141 is attached to the trigger wire release mechanism 166. Trigger wire release mechanism 166 is also part of the distal portion of the handle 129.

The stent graft 131 has diameter reducing tie arrangements to retain it in a partially diameter reduced condition even after the outer sheath 106 has been retracted during deployment. The diameter reducing tie arrangement is on each side of the stent graft and includes the trigger wire 160 stitched or otherwise coupled along the graft material on either side of the stent graft 131. Loops of filament such as suture thread 227 engaged around the trigger wire 160 and a portion of the graft material partly around the stent graft and then the loops are drawn tight.

FIG. 13 shows detail of the retention system 250 by which the guide wires 138 (for instance) is stabilized proximally of the fenestration 147 (for instance). The guide wire 138 may have a protrusion 252, which may be fastened with respect to the guide wire by solder, crimping, welding or gluing. A suture thread 254 may include one or more loops 254b that are looped around the guide wire 138 distally of the protrusion 252 and around a release wire 256. The release wire 256 may be stitched through the material of the stent graft 131 and then the suture thread 254 may be sewn at the loops 254a into the material of the stent graft 131. When the release wire 256 is retracted, the loop 254b of the suture thread 254 is released and the guide wire 138 can be retracted. In the meantime, the retention system stabilizes the guide wire.

FIG. 14 shows a cross section of a simple fenestration in cross section with the stabilized auxiliary guide wire extending through it. In this embodiment, the fenestration 260 is reinforced with a ring of resilient wire such as nitinol wire. The auxiliary guide wire 138 passes through the fenestration and is restrained just proximal of the fenestration using a retention system 250 as shown in FIG. 13.

FIG. 15 shows a cross section of an alternative fenestration arrangement incorporating a low profile side arm with the stabilized auxiliary guide wire extending through it. In this arrangement, the fenestration is in the form of a low profile side arm 264. The low profile side arm 264 has an inner portion 266, which extends within the tubular body of the stent graft 131, and an outer portion 268, which extends outside of the tubular body of the stent graft and is stitched into the periphery of the fenestration. The stitching extends circumferentially and diagonally from one end of the low profile side arm to the other. The fenestration in the form of the side arm 264 is shown at the stage of deployment at which the first access sheath 118 has been advanced over the auxiliary guide wire 138 until it just extends out of the low profile side arm 264. The auxiliary guide wire 138 passes through the fenestration and is restrained just proximal of the fenestration using the retention system 250 to stabilize the access sheath 118 while catheterization of a side branch artery is occurring. The dilator has been retracted and another guide wire 270 has been deployed through the access sheath 118 and this guide wire be used to catheterize the side branch artery.

Figure 16:
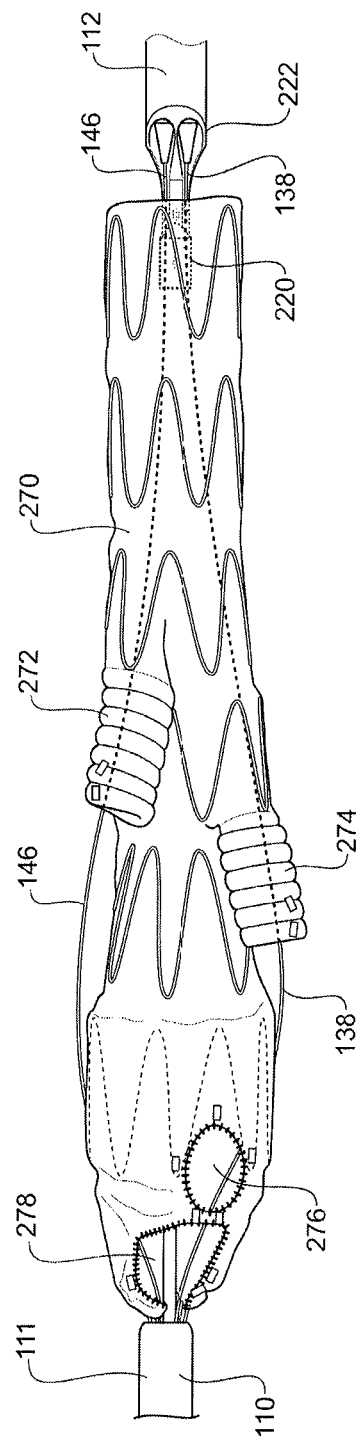
FIG. 16 shows an alternative embodiment of stent graft on a delivery device.

FIG. 16 shows an alternative embodiment of stent graft on a delivery device. Here, the stent graft 270 includes one or more side arms (shown as two high flexibility side arms 272 and 274) which are intended for connection to respective renal arteries, a fenestration 276 for the celiac artery, and a scalloped proximal end 278 for the superior mesenteric artery. The auxiliary guide wires 138 and 146 extend from the pusher catheter 112 within the stent graft 270 and pass out through the respective two high flexibility side arms 274 and 272 and are then stitched into the graft material to extend into capsule 111 on the nose cone dilator 110a. The stitching into the stent graft material proximally of the open ends of the two high flexibility side arms 272 and 274 assists in stabilization of the side arms during the catheterization of the renal arteries.

Returning to FIGS. 1-2, the body 114c of the manifold 114 defines a manifold side port 280 or a first fluid port. A first fluid connector 282 is shown attached within the manifold side port 280 and extending away from the manifold body 114c. A first fluid passageway 284 is defined by the first fluid connector 282. The manifold body 114c also defines a manifold passageway 286 through which the pusher catheter 112 that is coaxially disposed over the guide wire catheter 172. A hemostatic seal 288 is placed within the manifold passageway 286 sealably contacting between the inner wall 286a of the manifold passageway 286 and the outer surface of the guide wire catheter 172. The body of the pusher catheter 112 may define proximal end openings 290, 292, 294 for the 90, 92, 94 lumens, as shown in FIG. 9. In one example, the proximal end openings 290, 292, 294 may be located at the distal facing surface 295 of the pusher catheter 112.

The first fluid connector 282 may include a fluid conduit 296 extending from the first fluid connector 282 to a first luer valve 298. The first luer valve 298 includes a luer fitting end 300 and a valve section 302. The valve section 302 is configured for selective flow (0 to 100%) to the first fluid connector 282. The valve section 302 is shown have a stopcock configuration, but may include other configuration such as a gate or other ball valve configurations. The valve and its position within the valve section 302 may be manually controlled by a rotatable handle 304.

To enable flushing fluid and radiopaque medium to be deployed through the delivery device, a first fluid source containing a first flushing fluid may be coupled to the luer fitting end 298 (shown as a female end). With the valve open, the first flushing fluid, represented by arrows A, may enter within the first luer valve 298, traversing through the fluid conduit 296, the first fluid passageway 284 of the first fluid connector 282 and into the manifold passageway 286. The proximal end openings 290, 292, 294, the manifold passageway 286 and the first fluid passageway 284 are all in fluid communication. To this end, the first flushing fluid enters within the lumens 90, 92, 94 into annular spaces defined by the lumen walls and the outer surface of the outermost components. With reference to FIG. 8, first and second annular spaces 306, 308 are defined by the luminal wall of the respective lumens 92, 94 and the outer surfaces of the access sheaths 118, 122. A third annular space 310 is defined by the luminal wall of the lumen 90 and the outer surfaces of the retrieval catheter 127 and various trigger wires. With reference to FIGS. 1, 2, and 10D, the first flushing fluid exits the annular spaces 306, 308, 310 through the respective proximal end openings 290, 292, 294 of the corresponding lumens 90, 92, 94 and enters into the stent retention region 107 and fills the region 107. For certain fluids, after filling the operator will notice leakage of fluid from the proximal end 106a of the outer sheath 106 along the outer surface of the capsule 111.

Returning to FIGS. 1-2, the body 108a of the sheath hub 108 defines a hub side port 320, or a second fluid port, having a second fluid connector fitting 322 formed at the port 320, extending away from the sheath hub body 108a. A second fluid passageway 324 is defined by the hub side port body 320. The hub body 108a also defines a hub passageway 326 through which the pusher catheter 112 extends and is coaxially disposed over the guide wire catheter 172. A hemostatic seal 328 is placed within the hub passageway 326 sealably contacting between the inner wall 326a of the hub passageway 286 and the outer surface of the pusher catheter 112.

A fluid conduit 330 extends from the second fluid connector fitting 322 to a second luer valve 332. The second luer valve 332 includes a luer fitting end 334 and a valve section 336. The valve section 336 is configured for selective flow (0 to 100%) to the hub side port 320. The valve section 336 is shown have a stopcock configuration, but may include other configuration such as a gate or other ball valve configurations. The valve and its position within the valve section 336 may be manually controlled by a rotatable handle 338. To enable flushing fluid and radiopaque medium to be deployed through the delivery device, a second fluid source containing a second flushing fluid may be coupled to the luer fitting end 334 (shown as a female end). With the valve open, the second flushing fluid, represented by arrows B, may enter within the second luer valve 332, traversing through the fluid conduit 330, the second fluid passageway 324 and into the hub passageway 326. The distal end 106b of the outer sheath 106 is shown coupled around a proximal extension 340 extending proximally from the sheath hub 108 via a cap 342. This coupling is located proximal to the second fluid passageway 324. To this end, the second flushing fluid enters within an annular space 344 defined between the lumen walls of the outer sheath 106 and the outer surface of the pusher catheter 112. With reference to FIGS. 1 and 2, the second flushing fluid exits the annular space 344 at a location coinciding with the proximal end of the pusher catheter 112, enters into the stent retention region 107 and fills the region 107. For certain fluids, after filling the operator will notice leakage of fluid from the proximal end 106a of the sheath 106 along the outer surface of the capsule 111.

Returning to FIGS. 1-2, the luer connector 174, or a third fluid port, at the distal end of the guide wire catheter 172 defines a third fluid passageway 350. The luer connector 174 includes a luer fitting end 352. A third fluid source containing a third flushing fluid may be coupled to the luer fitting end 352 (shown as a female end). The third flushing fluid, represented by arrows C, may enter within the luer connector 174, traversing through the third fluid passageway 324 and into the lumen 354 of the guide wire catheter 172. The third flushing fluid exits the lumen 354 at the proximal end 355 of the guide wire catheter 172. For certain fluids, the operator will notice leakage of fluid from the proximal end 355.

The fluids may include a variety of fluids. The fluid may include a liquid flushing solution, such as saline, isomolar solutions, at least partially degassed solutions such as perflurochemicals, or other liquids having high solubility of respiratory gases. Saline may include 0.9% NaCl, heparinized saline, balanced salt solutions saline, or other flushing solutions. The source of the fluids may be a syringe, a bag of fluid, a fluid pump with a fluid line, or the like having a suitable mating connector for the luer fitting ends. The fluid may include a blood soluble gas, such as carbon dioxide ($CO_2$) or nitrous oxide, which may be effective for the removal of air from the delivery device. Other gases having suitable blood gas solubility may be used, such as helium argon or other bio-inert gases. A source of blood soluble gas is provided in a pressurized canister, which may be located in the room or remotely. A gas conduit having a mating connector suitable for the luer fitting ends may be provided. The pressure and flow of the blood soluble gas may be controlled, as is known.

Methods of reducing air within a stent graft delivery device via flushing the delivery device will now be described. In a first method, associated with Group A in the Table 1 below, the following steps are involved. Flushing associated with the manifold and the pusher catheter lumen is not utilized, and thus the first luer valve 298 is in the closed position. After coupling the second fluid source containing the second flushing fluid (20 ml of 0.9% saline) to the luer fitting end 334, the second flushing fluid enters within the second luer valve 332 (in open position), traversing through the fluid conduit 330, the second fluid passageway 324 and into the hub passageway 326. The second flushing fluid exits the annular space 344 at a location coinciding with the proximal end of the pusher catheter 112, enters into the stent retention region 107 and fills the region 107. The operator should notice leakage of saline from the proximal end 106a of the sheath 106 along the outer surface of the capsule 111. The second luer valve 332 may be closed. The third fluid source containing the third flushing fluid (20 ml of 0.9% saline) is coupled to the luer fitting end 352. The third flushing fluid enters within the luer connector 174, traversing through the third fluid passageway 324 and into the lumen 354 of the guide wire catheter 172. At least a partial amount of the third flushing fluid exits the lumen 354 at the proximal end 355 of the guide wire catheter 172. The operator should notice leakage of saline from the proximal end 355. After the two flushing steps, the delivery device is placed in a resting position for a period of time of 10 minutes. The rest period is to allow the flushing fluids to settle.

In a second method, associated with Group B in the Table 1 below, the following steps are involved; including all of the steps of the first method, except the second flushing fluid amount is increased to 60 ml of 0.9% saline. After the two flushing steps, the delivery device is placed in a resting position for a period of time of 10 minutes.

In a third method, associated with Group C in the Table 1 below, the following steps are involved, including all of the steps of the first method, except for the following. Prior to flushing with the second flushing fluid comprised of 20 ml of 0.9% saline, a blood soluble gas is used for flushing. Here, another fluid source containing another flushing fluid comprising $CO_2$ is coupled to the luer fitting end 334. The $CO_2$ is provided from a $CO_2$ gas cylinder with a reduction valve providing a pressure of 1.2 bar. The $CO_2$ enters within the second luer valve 332 (in open position), traversing through the fluid conduit 330, the second fluid passageway 324 and into the hub passageway 326. The $CO_2$ exits the annular space 344 at a location coinciding with the proximal end of the pusher catheter 112, enters into the stent retention region 107 and fills the region 107. At least a partial amount of $CO_2$ may exit the proximal end 106a of the sheath 106 along the outer surface of the capsule 111. The $CO_2$ is delivered to the stent delivery device for a period of time of at least two minutes. In the third method, a period of time of five minutes was used. Additional time may be added. Here, the sheath is flushed initially with a blood soluble gas and then with a saline solution. The guide wire catheter 172 is flushed with a saline solution. After the three flushing steps, the delivery device is placed in a resting position for a period of time of 10 minutes. The rest period is to allow the flushing fluids to settle and permit enough time for the flushing fluid to dissolve any remaining $CO_2$.

In a fourth method, associated with Group D in the Table 1 below, the following steps are involved. The first fluid source containing the first flushing fluid (20 ml of 0.9% saline) may be coupled to the luer fitting end 298. With the second luer valve 332 in the closed position, the first flushing fluid enters within the first luer valve 298 (in the open position), traversing through the fluid conduit 296, the first fluid passageway 284 of the first fluid connector 282 and into the manifold passageway 286. The first flushing fluid enters within the lumens 90, 92, 94 into the annular spaces 306, 308, 310 and exits the annular spaces 306, 308, 310 through the respective proximal end openings 290, 292, 294, where it enters into the stent retention region 107 and fills the region 107. The operator should notice leakage of saline fluid from the proximal end 106a of the outer sheath 106. Following this step, the steps of the second method step with the second flushing fluid amount of 60 ml of 0.9% saline is used to flush the sheath. Here, the pusher catheter is flushed with a saline solution, initially, and then the sheath is flushed with a saline solution is greater quantities than the pusher catheter. The guide wire catheter 172 is flushed with a saline solution. After the three flushing steps, the delivery device is placed in a resting position for a period of time of 10 minutes.

In a fifth method, associated with Group E in the Table 1 below, the following steps are involved, including all of the steps of the fourth method, except the following. Prior to flushing with the second flushing fluid comprised of 60 ml of 0.9% saline, a blood soluble gas is used for flushing. Here, another fluid source containing another flushing fluid comprising CO2 is coupled to the luer fitting end 334. The CO2 enters within the second luer valve 332 (in open position), traversing through the fluid conduit 330, the second fluid passageway 324 and into the hub passageway 326. The CO2 exits the annular space 344 at a location coinciding with the proximal end of the pusher catheter 112, enters into the stent retention region 107 and fills the region 107, exiting the proximal end 106*a* of the sheath 106 along the outer surface of the capsule 111. The CO2 is delivered to the stent delivery device for a period of time of at least two minutes, and preferably, five minutes. Here, the pusher catheter is flushed with a saline solution, initially. Then, the sheath is flushed initially with a blood soluble gas and then with a saline solution, in greater quantities than the pusher catheter. The guide wire catheter 172 is flushed with a saline solution. After the four flushing steps, the delivery device is placed in a resting position for a period of time of 10 minutes. The rest period is to allow the flushing fluids to settle and permit enough time for the flushing fluid to dissolve any remaining CO2.

Other methods are contemplated. For example, another fluid source comprising a blood soluble gas may be flushed within the first luer valve 298 (in the open position), traversing through the fluid conduit 296, the first fluid passageway 284 of the first fluid connector 282 and into the manifold passageway 286. The first flushing fluid enters within the lumens 90, 92, 94 into the annular spaces 306, 308, 310 and exits the annular spaces 306, 308, 310 through the respective proximal end openings 290, 292, 294, where it enters into the stent retention region 107 and fills the region 107. A gas flushing may also occur within the guide wire lumen. Each of these gas flushings may occur prior to the saline flushing steps.

Figure 17:
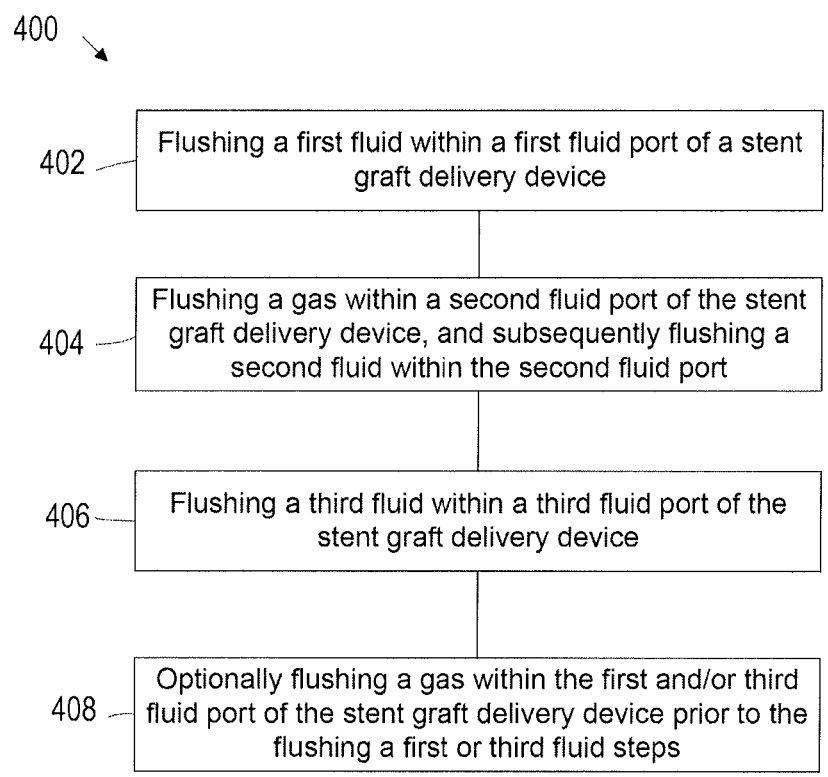
FIG. 17 is a flow diagram depicting a method of reducing air in a stent graft delivery device.

In an example, a method of reducing air within a stent graft delivery device, referenced as 400, is shown in FIG. 17. In step 402, a first fluid is flushed within the first fluid port of the stent graft delivery device. In step 404, a gas is flushed within the second fluid port of the stent graft delivery device, and subsequently, as a second fluid is flushed within the second fluid port. In step 406, a third fluid is flushed within a third port of the stent graft delivery device. In optional step 408, a gas may be flushed within the first and/or the third fluid port prior to the flushing a first or third fluid steps.

The test results were obtained by the following test protocol. The testing system includes a container of water or liquid and an L-shaped conduit. One end of the conduit is placed along the container bottom and the elevated end extends in an upright position from the container outside the water. The elevated end may be comprised of a tapered portion funneling inward. An additional inward funnel may be coupled between the elevated end and a fluid measurement device, such as, for example, a syringe. A stopcock valve may be disposed between the elevated end and the fluid measurement device for selective communication between the components. In one example, the additional inward funnel may include threaded ends for attachment to the fluid measurement device and to the elevated end. Air is initially removed from the testing system or a reference point of air is created via a vacuum device, such as a syringe or pump, prior to introducing the stent graft delivery device. For example, a 10 ml syringe may be coupled to the elevated end via the stopcock valve and the plunger of the piston may be pulled to move water within the conduit toward the elevated end. In one aspect, the water level within the conduit may be set at the end of the syringe. In another aspect, the water level within the conduit may be set at other locations such as the entry of the valve. With the valve closed, the 10 ml syringe may be removed from the elevated end and replaced with a 2 ml syringe or other device for finer measurement capability.

After each of the methods described herein were performed, including resting for a period of time of 10 minutes, the stent graft delivery device is inserted into the conduit end submerged in water and placed upright within the conduit. Water may enter the stent graft delivery device in a manner to start from the distal end and fill the device from the distal end to the proximal end, thereby pushing air out of the proximal end into the conduit into the funneled portions. As a result of the device air being introduced to the testing system, air will rise to the top and cause the water level to drop below the reference point. With the fluid measurement device such as a syringe attached, the plunger of the syringe, starting at the bottom, is pulled in order to remove device air from the conduit until water reaches the reference point. The location of the piston relative to the barrel of the syringe is noted as an indication of the measured amount of remaining air within the stent graft delivery device after utilizing the flushing techniques.

In another testing system example, after each of the methods described herein were performed, including resting for a period of time of 10 minutes, a distal end of a conduit, such as a flexible membrane or rigid tube, is sealably coupled along the outer sheath distal to the proximal end of the outer sheath. The conduit may be made of a transparent material to allow visible indication within the conduit. A fluid port is provided with the conduit, which is configured for sealably coupling with a fluid measurement device. For example, the fluid port includes a female luer fitting configuration for coupling to a fluid measurement device that is a syringe. As much air as possible is removed out of the conduit before attachment. After attachment and with the piston of the syringe at its bottom end, the plunger of the syringe is pulled in order to remove any remaining air from the conduit. Air may be removed by another type of vacuum device fluidly coupled to the conduit. This first location of the piston relative to the barrel of the syringe is noted and marked.

In an example, another syringe may be coupled to the fluid port of the conduit and used to evacuate air remaining in the conduit. The fluid port of the conduit may include a valve section to allow for the closure of the fluid port for exchanging the syringes. For the final measurement, a syringe, for example, a 2 ml syringe, is coupled to the fluid port.

With the stent graft delivery device in an upright position with the nose cone dilator in the top position, the distal end of the stent graft delivery device is introduced to a water bath. The stent graft delivery device in its upright position is slowly lowered into the water bath allowing the water to enter into the device and push air upwards toward the conduit and filling the conduit with the remaining air from the device. An indication of complete air removal from the stent graft delivery device is when water begins to be introduced into the conduit. At such indication, the stent graft delivery device is maintained at its upright position and no longer lowered. The plunger of the syringe is pulled in order to remove any remaining air from the conduit until water contacts the tip of the syringe. This second location of the piston relative to the barrel of the syringe is noted and marked. The difference between the first location marked and the second location marked provides an indication of the amount of remaining air within the stent graft delivery device after utilizing the flushing techniques.

Figure 18:
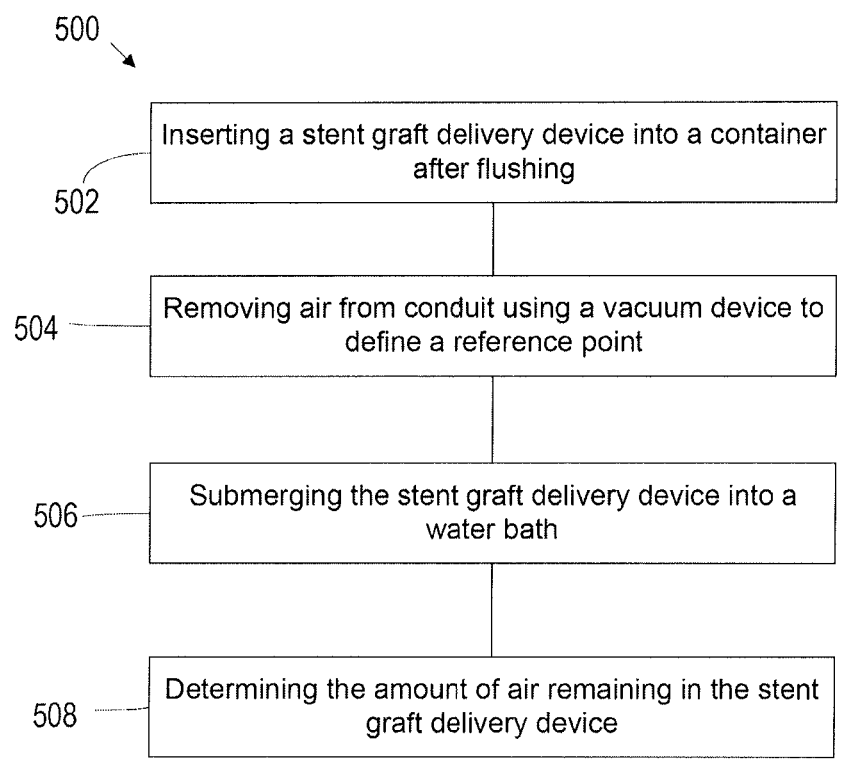
FIG. 18 is a flow diagram depicting a method of determining an amount of air in a flushed stent graft delivery device.

In an example, a method of determining an amount of air within a flushed stent graft delivery device is provided, referenced as 500, as shown in FIG. 18. In step 502, a stent graft delivery device is inserted into a conduit after being initially flushed utilizing a flushing technique. In step 504, air is removed from the container using a vacuum device, such as, for example, a syringe or vacuum pump, to define a reference point. In step 506, the stent graft delivery device is submerged into a fluid bath, such as water, such that device air is forced out of the device into the conduit. In step 508, an amount of air remaining in the flushed stent graft delivery device is determined or measured, as described above.

The test protocol is performed multiple times for each of the methods and data obtained to develop statistical significance. Table 1 shows improvement from the first method associated with group A to the fifth method associated with group E. A vast improvement of air reduction is achieved as a result of the fifth method associated with group E, with less than 0.2 ml, and in an example less than 0.14 ml (0.07±0.07 ml), of air present after the flushing technique. By comparison with group D, over eighty percent of more air was removed with the additional step of gas flushing through the sheath fluid port. By comparison with group C, over eighty percent of more air was removed with the additional step of saline flushing through the manifold fluid port and the increased saline flushing through the sheath fluid port after the gas flushing. By comparison with group B, over ninety percent of more air was removed with the additional step of saline flushing through the manifold fluid port and the increased saline flushing through the sheath fluid port. By comparison with group A, over ninety-four percent of more air was removed with the additional step of saline flushing through the manifold fluid port, the increased saline flushing through the sheath fluid port, and the gas flushing through the sheath fluid port prior the saline flushing.

TABLE 1

Delivery Device Flushing Methods and Results

| Group | Flushing Protocol | Remaining Air in System (ml) |
|---|---|---|
| A | 1. Flush sheath with 20 ml saline<br>2. Flush guide wire catheter with saline<br>3. Rest for ten minutes | 1.23 ± 0.74 |
| B | 1. Flush sheath with 60 ml saline<br>2. Flush guide wire catheter with saline<br>3. Rest for ten minutes | 0.79 ± 0.20 |
| C | 1. Flush sheath with CO2 for five mins.<br>2. Flush sheath with 20 ml saline<br>3. Flush guide wire catheter with saline<br>4. Rest for ten minutes | 0.51 ± 0.19 |
| D | 1. Flush pusher catheter with 20 ml saline<br>2. Flush sheath with 60 ml saline<br>3. Flush guide wire catheter with saline<br>4. Rest for ten minutes | 0.51 ± 0.10 |
| E | 1. Flush pusher catheter with 20 ml saline<br>2. Flush sheath with CO2 for five mins.<br>3. Flush sheath with 60 ml saline<br>4. Flush guide wire catheter with saline<br>5. Rest for ten minutes | 0.07 ± 0.07 |

After the flushing steps, the introduction steps may occur. The introduction part 104 of the delivery device 100 may be introduced into the aorta correctly taking into account N-S position as well as rotational position with respect to target vessels and fenestrations on the stent graft 131 using markers on stent graft body. At this stage, the delivery device is as shown in FIGS. 1-2. Withdraw the outer sheath 106 of the delivery device while continuing to check position until the distal end 145 of the stent graft 131 opens. At this stage the distal end 145 of the stent graft 131 is still retained by distal fixation, for example as shown in FIG. 3, the proximal end of the stent graft is retained by the exposed stent 137 being retained in the capsule 111 of the delivery device and the expansion of the stent graft is restricted by the diameter reducing ties. This stage is shown in part in FIG. 12.

The access sheaths 118, 122 (left and right) are advanced on their respective indwelling guide wires 138, 146 through the lumen of stent graft 131 to or through the fenestration 147 (at this stage the capsule retains the exposed stent and the indwelling guide wires). The first access sheath is positioned at the opening of the fenestration. The dilator 134 of the first access sheath is removed.

An additional catheter and additional guide wire (4-5 Fr) is advanced through the first access sheath and into the target vessel (e.g. renal artery). The additional catheter may have a crooked or hockey stick tip to facilitate access. The guide wire is removed from the additional catheter and a stiffer wire is re-inserted into the target vessel.

The stabilization retention system 250 of indwelling guide wires 138 is released via the trigger wire release 160. The indwelling wire guide is retrieved from the top capsule 111 and pulled out completely. The additional catheter is removed and the access sheath dilator and dilator catheter is re-placed over the stiffer wire into the target vessel and the access sheath is advanced over the stiffer wire into the target vessel. The access sheath dilator is then withdrawn. These steps may be repeated for the other of the target vessels.

Covered stents are advanced through each of the access sheaths into the target vessels but are not released. The diameter reducing ties are released by releasing and withdrawing the trigger wire release 162. The capsule 111 is released by removing the locking trigger wire 143 via trigger wire release 164, releasing the pin vice 170, and advancing the capsule on the guide wire catheter to release the top exposed stent. At the same time, the distally facing capsule moves proximally over the distal retrieval taper device to allow the distal retrieval taper device to extend from the distal end of the capsule. This stage is shown in FIG. 3.

Figure 4:
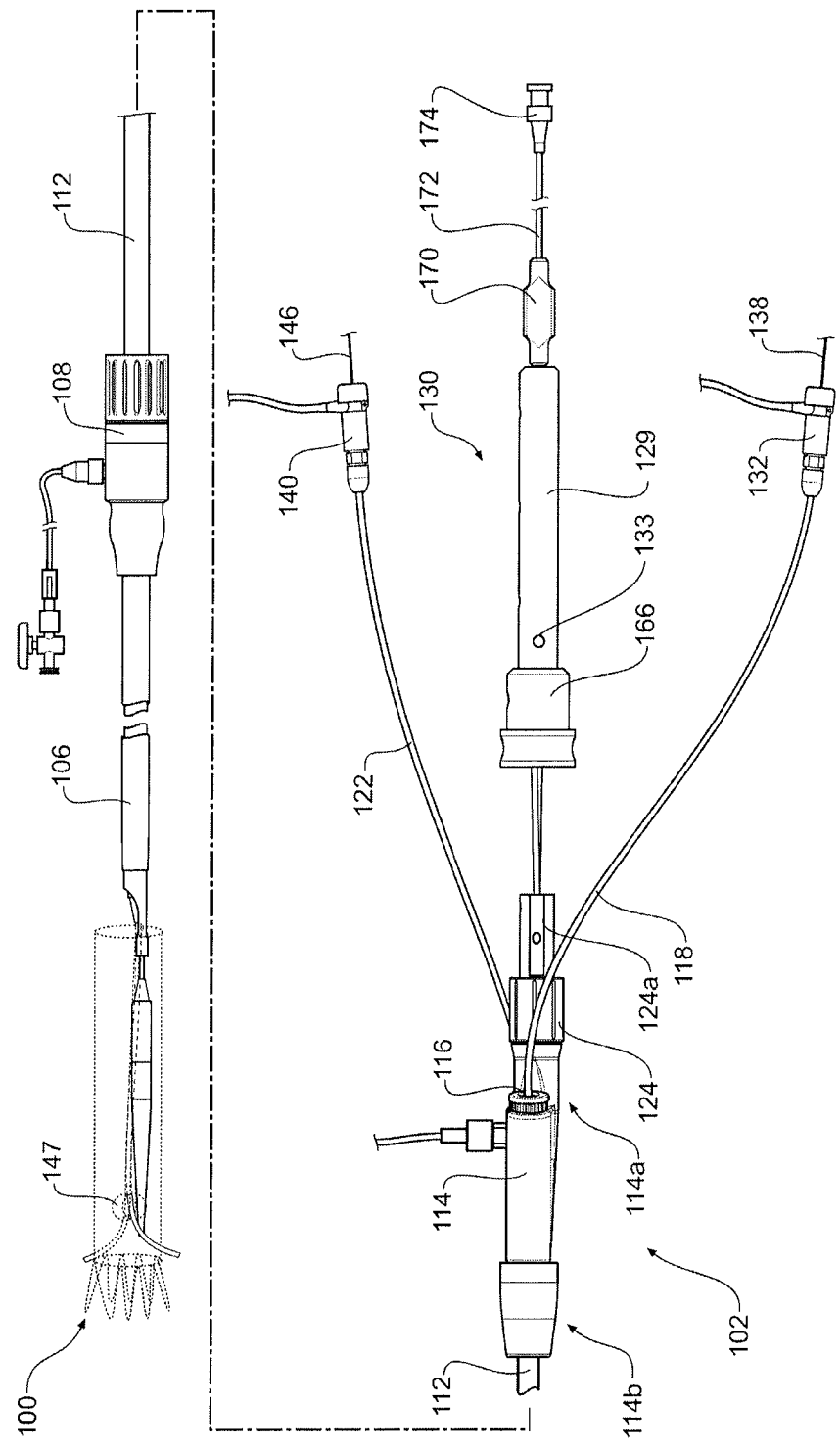
FIG. 4 in the stent graft delivery device of FIG. 1 in a further partially activated condition.

The pin vice 170 is tightened or locked. The nose cone dilator, top cap and distal retrieval taper may be distally retracted past the fenestration by removing the locking screw 125 of the distal handle portion and retracting distal portion of handle. This also releases the distal attachment via trigger wire 141 connected to trigger wire release 166. This stage is shown in FIGS. 4, 5 and 7.

One at a time, the access sheaths are withdrawn from the target vessels and covered stents are deployed between the fenestrations and target vessels. A balloon expanded device may be used to balloon expand if necessary for flaring portion of the covered stent within the fenestration of the main stent graft.

Access sheaths are then removed and the guide wires are also removed from the target vessels and withdrawn from the system. The nose cone dilator, top cap and distal retrieval taper to the sheath 106 are then retracted. The entire assembly may then be withdrawn or the outer sheath may be left in place for further deployments. Further deployment may include a bifurcated distal component.

It is seen that by this invention an arrangement is provided that by which access sheaths may extend through the introduction device and are able to be separately manipulated to enable access to renal or other arteries within the vasculature of a patient.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A method of reducing air within a stent graft delivery device, comprising;

providing a stent graft delivery device comprising a guide wire catheter, a pusher catheter coaxially disposed over the guide wire catheter, a pusher catheter lumen, the pusher catheter arranged relative to the guide wire catheter to define a stent graft retention region therebetween, a manifold including a manifold passageway longitudinally receiving the pusher catheter, a sheath hub including a hub passageway longitudinally receiving the pusher catheter, and a sheath arrangement longitudinally extending from the sheath hub toward a proximal end of the guide wire catheter, the sheath arrangement being coaxial with and surrounding the guide wire catheter and the pusher catheter, wherein a first fluid port is defined by the manifold and in communication with the manifold passageway and the pusher catheter lumen, a second fluid port is defined by the sheath hub and in communication with the hub passageway and an annular space defined between the sheath arrangement and the pusher catheter, and a third fluid port is at a distal end of the guide wire catheter and in communication with a guide wire lumen longitudinally extending within the guide wire catheter;

flushing a first liquid within the first fluid port, whereby the first liquid traverses the manifold passageway, traverses proximally through the pusher lumen, through a proximal end opening of the pusher catheter, and into the stent graft retention region, and at least a partial amount of first fluid exits the stent graft retention region at a proximal end of the sheath arrangement;

flushing a gas within the second fluid port, and after a period of time subsequently flushing a second liquid within the second fluid port, whereby each of the gas and the second liquid traverses the hub passageway, traverses proximally through the annular space and into the stent graft retention region, and at least a partial amount of gas and at least a partial amount of second fluid exit the stent graft retention region at the proximal end of the sheath arrangement;

flushing a third liquid within the third fluid port, whereby the third liquid traverses proximally through the guide wire lumen and at least a partial amount of third fluid exits out of the proximal end of the guide wire catheter, whereby less than 0.2 ml of air is present in the stent graft delivery device, and providing a rest period sufficient to dissolve any remaining gas.

2. The method of claim 1, wherein the first liquid, the second liquid, and third liquid comprise saline.

3. The method of claim 1, wherein an amount of the second liquid is greater than an amount of the first liquid.

4. The method of claim 1, wherein the gas comprises a blood soluble gas.

5. The method of claim 4, wherein the blood soluble gas comprises carbon dioxide.

6. The method of claim 4, wherein the second liquid comprises saline.

7. The method of claim 1, further comprising flushing a second gas within the first fluid port prior to the flushing a first liquid step, whereby the second gas traverses the manifold passageway, traverses proximally through the pusher lumen, through the proximal end opening of the pusher catheter, and into the stent graft retention region, and at least a partial amount of second gas exits the stent graft retention region at the proximal end of the sheath arrangement.

8. A method of reducing air within a stent graft delivery device, comprising;

providing a stent graft delivery device comprising a guide wire catheter, a dilator at a proximal end of the guide wire catheter, a pusher catheter coaxially disposed over the guide wire catheter, a pusher catheter lumen, a proximal end of the pusher catheter spaced distally from the dilator to define a stent graft retention region therebetween, a manifold longitudinally receiving the pusher catheter, a sheath hub longitudinally receiving the pusher catheter, and a sheath arrangement longitudinally extending from the sheath hub toward the dilator, the sheath arrangement being coaxial with and surrounding the guide wire catheter and the pusher catheter, wherein a manifold port is defined by the manifold and in communication with the pusher lumen, a sheath hub port is defined by the sheath hub and in communication with an annular space defined between the sheath arrangement and the pusher catheter;

flushing a first fluid within the manifold port, the first fluid traversing proximally through the pusher catheter lumen, the proximal end of the pusher catheter, and into the stent graft retention region, and exiting the stent graft retention region at a proximal end of the sheath arrangement;

flushing a second fluid within the sheath hub port, the second fluid comprising a blood soluble gas, the second fluid traversing proximally in the annular space and into the stent graft retention region, and exiting the stent graft retention region at the proximal end of the sheath arrangement;

flushing a third fluid within the sheath hub port, the third fluid traversing proximally in the annular space and into the stent graft retention region, and exiting the stent graft retention region at the proximal end of the sheath arrangement;

flushing a fourth fluid within a distal end opening of the guide wire catheter, the fourth fluid traversing proximally through a guide wire lumen that extends longitudinally within the guide wire catheter and exiting out of the proximal end of the guide wire catheter, whereby each of the flushing steps contribute to a removal of air present in the stent graft delivery device prior to the delivery of the stent graft delivery device into a patient; and providing a rest period sufficient to dissolve any remaining blood soluble gas.

9. The method of claim 8, further comprising closing access to the sheath hub port, prior to the flushing a first fluid step.

10. The method of claim 9, further comprising opening access to the sheath hub port and closing access to the manifold port, after the flushing a first fluid step and prior to the flushing a second fluid step.

11. The method of claim 10, wherein the first fluid, the second fluid, and the fourth fluid comprise liquid.

12. The method of claim 11, wherein an amount of the second fluid is greater than an amount of the first fluid.

13. The method of claim 11, wherein the blood soluble gas comprises carbon dioxide.

14. A method of reducing air within a stent graft delivery device, comprising;
provapparatus a stent graft delivery device comprising a guide wire catheter, a dilator at a proximal end of the guide wire catheter, a pusher catheter coaxially disposed over the guide wire catheter, a pusher catheter lumen, a proximal end opening of the pusher catheter spaced distally from the dilator to define a stent graft retention region therebetween, a manifold longitudinally receiving the pusher catheter, a sheath hub longitudinally receiving the pusher catheter, and a sheath arrangement longitudinally extending from the sheath hub toward the dilator, the sheath arrangement being coaxial with and surrounding the guide wire catheter and the pusher catheter, wherein a manifold port is defined by the manifold and in communication with the manifold passageway and the pusher lumen, a sheath hub port is defined by the sheath hub and in communication with the hub passageway and an annular space defined between the sheath arrangement and the pusher catheter;
introducing a first fluid of saline within the manifold port such that the first fluid of saline traverses the manifold passageway, proximally through the pusher catheter lumen, through the proximal end opening of the pusher catheter, and into the stent graft retention region, and exits the stent graft retention region at a proximal end of the sheath arrangement;
introducing a second fluid of carbon dioxide within the sheath hub port such that the second fluid of carbon dioxide traverses the hub passageway and proximally in the annular space, and into the stent graft retention region, and exits the stent graft retention region at the proximal end of the sheath arrangement;
introducing a third fluid of saline within the sheath hub port after the introducing a second fluid of carbon dioxide step such that the third fluid of saline traverses the hub passageway, proximally in the annular space, and into the stent graft retention region, and exits the stent graft retention region at the proximal end of the sheath arrangement;
introducing a fourth fluid of saline within a distal end opening of the guide wire catheter such that the fourth fluid of saline traverses proximally through a guide wire lumen that longitudinally extends within the guide wire catheter and exits out of the proximal end of the guide wire catheter, whereby less than 0.14 ml of air is present in the stent graft delivery device; and
providing a rest period sufficient to dissolve any remaining carbon dioxide.

15. The method of claim 14, wherein the introducing a first fluid of saline step occurs prior to the introducing a second fluid of carbon dioxide.

16. The method of claim 15, further comprising closing access to the sheath hub port, prior to the introducing a first fluid of saline step.

17. The method of claim 16, further comprising opening access to the sheath hub port and closing access to the manifold port, after the introducing a first fluid of saline step and prior to the introducing a second fluid of carbon dioxide step.

18. The method of claim 15, wherein an amount of the first fluid of saline is less than an amount of the third fluid of saline.

19. The method of claim 15, wherein the introducing a second fluid of carbon dioxide has a duration of five minutes.

20. The method of claim 19, further comprising maintaining a rest position for the delivery device for a duration of ten minutes, after the introducing a first fluid of saline step, the introducing a second fluid of carbon dioxide step, the introducing a third fluid of saline step, and the introducing a fourth fluid of saline step.

21. A method of reducing air within a stent graft delivery device, comprising;
providing a stent graft delivery device comprising a guide wire catheter, a pusher catheter coaxially disposed over the guide wire catheter, a pusher catheter lumen, the pusher catheter arranged relative to the guide wire catheter to define a stent graft retention region therebetween, a manifold including a manifold passageway longitudinally receiving the pusher catheter, a sheath hub including a hub passageway longitudinally receiving the pusher catheter, and a sheath arrangement longitudinally extending from the sheath hub toward a proximal end of the guide wire catheter, the sheath arrangement being coaxial with and surrounding the guide wire catheter and the pusher catheter, wherein a first fluid port is defined by the manifold and in communication with the manifold passageway and the pusher catheter lumen, a second fluid port is defined by the sheath hub and in communication with the hub passageway and an annular space defined between the sheath arrangement and the pusher catheter, and a third fluid port is at a distal end of the guide wire catheter and in communication with a guide wire lumen longitudinally extending within the guide wire catheter;
first, flushing a first liquid within the first fluid port, whereby the first liquid traverses the manifold passageway, traverses proximally through the pusher lumen, through a proximal end opening of the pusher catheter, and into the stent graft retention region, and at least a partial amount of first fluid exits the stent graft retention region at a proximal end of the sheath arrangement;
after flushing the first fluid port with the first liquid, flushing a gas within the second fluid port, and after a period of time subsequently flushing a second liquid within the second fluid port, whereby each of the gas and the second liquid traverses the hub passageway, traverses proximally through the annular space and into the stent graft retention region, and at least a partial amount of gas and at least a partial amount of second fluid exit the stent graft retention region at the proximal end of the sheath arrangement;
flushing a third liquid within the third fluid port, whereby the third liquid traverses proximally through the guide wire lumen and at least a partial amount of third fluid exits out of the proximal end of the guide wire catheter, whereby less than 0.2 ml of air is present in the stent graft delivery device; and
providing a rest period sufficient to dissolve any remaining gas.

22. A method of reducing air within a stent graft delivery device, comprising the steps of:
providing a stent graft delivery device comprising a guide wire catheter, a dilator at a proximal end of the guide wire catheter, a pusher catheter coaxially disposed over the guide wire catheter, a pusher catheter lumen, a proximal end of the pusher catheter spaced distally from the dilator to define a stent graft retention region therebetween, a manifold longitudinally receiving the pusher catheter, a sheath hub longitudinally receiving the pusher catheter, and a sheath arrangement longitudinally extending from the sheath hub toward the dilator, the sheath arrangement being coaxial with and surrounding the guide wire catheter and the pusher catheter, wherein a manifold port is defined by the manifold and in communication with the pusher lumen, a sheath hub port is defined by the sheath hub and in communication with an annular space defined between the sheath arrangement and the pusher catheter;

first, flushing a first fluid within the manifold port, the first fluid traversing proximally through the pusher catheter lumen, the proximal end of the pusher catheter, and into the stent graft retention region, and exiting the stent graft retention region at a proximal end of the sheath arrangement;

next, flushing a second fluid within the sheath hub port, the second fluid comprising a blood soluble gas, the second fluid traversing proximally in the annular space and into the stent graft retention region, and exiting the stent graft retention region at the proximal end of the sheath arrangement;

then, flushing a third fluid within the sheath hub port, the third fluid traversing proximally in the annular space and into the stent graft retention region, and exiting the stent graft retention region at the proximal end of the sheath arrangement;

at some point in the steps of the method, flushing a fourth fluid within a distal end opening of the guide wire catheter, the fourth fluid traversing proximally through a guide wire lumen that extends longitudinally within the guide wire catheter and exiting out of the proximal end of the guide wire catheter, whereby the flushing steps contribute to a removal of air present in the stent graft delivery device; and providing a rest period sufficient to dissolve any remaining blood soluble gas.

23. A method of reducing air within a stent graft delivery device, comprising the steps of:

providing a stent graft delivery device comprising a guide wire catheter, a dilator at a proximal end of the guide wire catheter, a pusher catheter coaxially disposed over the guide wire catheter, a pusher catheter lumen, a proximal end opening of the pusher catheter spaced distally from the dilator to define a stent graft retention region therebetween, a manifold longitudinally receiving the pusher catheter, a sheath hub longitudinally receiving the pusher catheter, and a sheath arrangement longitudinally extending from the sheath hub toward the dilator, the sheath arrangement being coaxial with and surrounding the guide wire catheter and the pusher catheter, wherein a manifold port is defined by the manifold and in communication with the manifold passageway and the pusher lumen, a sheath hub port is defined by the sheath hub and in communication with the hub passageway and an annular space defined between the sheath arrangement and the pusher catheter;

introducing a first fluid of saline within the manifold port such that the first fluid of saline traverses the manifold passageway, proximally through the pusher catheter lumen, through the proximal end opening of the pusher catheter, and into the stent graft retention region, and exits the stent graft retention region at a proximal end of the sheath arrangement;

next, introducing a second fluid of carbon dioxide within the sheath hub port such that the second fluid of carbon dioxide traverses the hub passageway and proximally in the annular space, and into the stent graft retention region, and exits the stent graft retention region at the proximal end of the sheath arrangement;

then, introducing a third fluid of saline within the sheath hub port after the introducing a second fluid of carbon dioxide step such that the third fluid of saline traverses the hub passageway, proximally in the annular space, and into the stent graft retention region, and exits the stent graft retention region at the proximal end of the sheath arrangement;

at some point in the steps of the method, introducing a fourth fluid of saline within a distal end opening of the guide wire catheter such that the fourth fluid of saline traverses proximally through a guide wire lumen that longitudinally extends within the guide wire catheter and exits out of the proximal end of the guide wire catheter, whereby less than 0.14 ml of air is present in the stent graft delivery device; and providing a rest period sufficient to dissolve any remaining carbon dioxide.

* * * * *